(12) United States Patent
Adelholt

(10) Patent No.: US 11,471,305 B2
(45) Date of Patent: Oct. 18, 2022

(54) COUPLING DEVICE FOR PROSTHESIS

(71) Applicant: C LindheXtend AB, Halmstad (SE)

(72) Inventor: Martin Adelholt, Västerås (SE)

(73) Assignee: C LindheXtend AB, Halmstad (SE)

( * ) Notice: Subject to any disclaimer, the term of this patent is extended or adjusted under 35 U.S.C. 154(b) by 0 days.

(21) Appl. No.: 17/253,936

(22) PCT Filed: Jun. 17, 2019

(86) PCT No.: PCT/SE2019/000008
§ 371 (c)(1),
(2) Date: Dec. 18, 2020

(87) PCT Pub. No.: WO2019/245419
PCT Pub. Date: Dec. 26, 2019

(65) Prior Publication Data
US 2021/0267774 A1 Sep. 2, 2021

(30) Foreign Application Priority Data
Jun. 19, 2018 (SE) .................................. 1830198-6

(51) Int. Cl.
*A61F 2/60* (2006.01)
*A61F 2/50* (2006.01)

(52) U.S. Cl.
CPC .................. *A61F 2/50* (2013.01); *A61F 2/60* (2013.01); *A61F 2002/5001* (2013.01); *A61F 2002/5083* (2013.01)

(58) Field of Classification Search
CPC ...... A61F 2/50; A61F 2/60; A61F 2002/5001; A61F 2002/5083; A61F 2002/608; A61F 2002/607
See application file for complete search history.

(56) References Cited

U.S. PATENT DOCUMENTS

| 4,564,365 A | 1/1986 | Winer et al. |
| 4,608,054 A | 4/1986 | Schroder |
| 5,326,352 A | 7/1994 | Ferrier |

(Continued)

FOREIGN PATENT DOCUMENTS

| DE | 20 2018 000 520 | 5/2018 |
| SE | 446373 | 9/1986 |

(Continued)

*Primary Examiner* — Bruce E Snow
(74) *Attorney, Agent, or Firm* — Renner, Otto, Boisselle & Sklar, LLP

(57) ABSTRACT

A coupling device, for connecting at least one first prosthetic part with at least one second prosthetic part of which at least one of the prosthetic parts is provided with, alternatively is suitable to be provided with, cosmetics. The coupling device comprises at least one first coupling part and at least one second coupling part which are suitable for connection to each other and in a connected position are temporarily locked to each other with at least one locking device. The coupling parts are disengaged from each other with at least one disengaging device. The first coupling part comprises at least one first holder for cosmetics and the second coupling part comprises at least one second holder for cosmetics. The cosmetics are attached to, alternatively integrated with, at least one of the first holder for cosmetics and the second holder for cosmetics.

13 Claims, 26 Drawing Sheets

(56) References Cited

U.S. PATENT DOCUMENTS

| | | | |
|---|---|---|---|
| 5,435,604 A | 7/1995 | Chen | |
| 6,361,569 B1 | 3/2002 | Slemker et al. | |
| 6,626,951 B1 * | 9/2003 | Gramnas | F16B 2/246 |
| | | | 292/306 |
| 6,679,921 B2 | 1/2004 | Grubbs | |
| 6,893,468 B2 * | 5/2005 | Lund | A61F 2/78 |
| | | | 623/36 |
| 6,981,992 B2 | 1/2006 | Curtis | |
| 7,081,138 B2 | 7/2006 | Hellberg | |
| 8,435,308 B2 * | 5/2013 | Atteraas | A61F 2/78 |
| | | | 623/32 |
| 8,591,599 B1 | 11/2013 | Kaliki et al. | |
| 9,155,635 B2 | 10/2015 | Radzinsky | |
| 9,956,093 B1 * | 5/2018 | Harris | A61F 2/76 |
| 10,828,180 B2 | 11/2020 | Granz | A61F 2/66 |
| 11,185,430 B2 * | 11/2021 | Hannesson | A61F 2/78 |
| 2012/0245707 A1 * | 9/2012 | Osgyan | A61F 2/76 |
| | | | 623/32 |
| 2017/0304086 A1 * | 10/2017 | Kuiken | A61F 2/54 |
| 2018/0363689 A1 | 12/2018 | Richter et al. | |
| 2019/0290453 A1 | 9/2019 | Fitz et al. | |
| 2020/0121477 A1 | 4/2020 | Lindhe et al. | |

FOREIGN PATENT DOCUMENTS

| | | |
|---|---|---|
| SE | 518263 | 9/2002 |
| WO | 2011117390 | 9/2011 |

* cited by examiner

COUPLING DEVICE FOR PROSTHESIS

This application is a national phase of International Application No. PCT/SE2019/000008 filed Jun. 17, 2019 and published in the English language, which claims priority to Swedish Application No. 1830198.6 filed Jun. 19, 2018, both of which are hereby incorporated herein by reference.

FIELD OF THE INVENTION

The present invention refers to a coupling device for prostheses in accordance with the claims.

BACKGROUND OF THE INVENTION

For various reasons, a number of people have amputated part of at least one of their extremities, such as an amputated part of a leg. For example, amputation may be caused by an accident, illness or other event. Lacking part of an extremity, as part of a leg, entails several problems. For example, the amputated persons mobility is usually diminished and the persons possibility of pursing different types of activities is limited.

In order to reduce the aforementioned problems for those who have been amputated, different variants of prostheses and similar aids have been developed. Even though several different types of prostheses have already been invented, there are still problems with the use of these earlier prostheses.

For example, problems exist with the coupling devices of prostheses. The coupling devices include at least one first coupling part and at least one second coupling part, with which the prosthesis and the limb of the person are connected. One problem with existing coupling devices is that it is cumbersome and time-consuming to connect and disconnect them. The coupling devices are many times of such design that they cannot be disconnected or connected only with the hands and hand power, they usually require tools to be connected and disconnected.

Another problem with known quick connect couplings is the presence of play between the first coupling part and the second coupling part of the coupling device. Play in the coupling device causes annoyance during use, especially in the case of walking and the like. Play propagates through the sleeve to the bone, which creates discomfort. Play also creates noise, for example, in the form of a clicking sound and vibrations which are irritating.

Another problem with prostheses, equipped with coupling devices, is to attach cosmetics (cosmetic covers) to the prosthesis without lessening the functionality of the prosthesis. Cosmetics usually consist preferably of foamed material enclosed in a silicone cover. The problem with cosmetics is that it impedes access to the coupling device's disengaging (release) mechanism, that is, the releasing device by which the first part of the coupling and the second part are disconnected. A problem with known designs of coupling mechanisms (devices) is that they require large recesses or holes in the cosmetics in order for the coupling mechanism to be connected together and disconnected. These recesses and/or the holes inhibit the main function of cosmetics to give a natural appearance.

PRIOR ART

The company Ferrier Couplers markets a number of variants of coupling devices for prostheses. Ferrier Coupler's coupling devices include a male member and a female member, which are connected together. Ferrier's coupling devices differ substantially from the coupling device in accordance with the present invention. For example, Ferrier's coupling devices require that tools be used to lock, and release, the female the male members.

Ferrier's U.S. Pat. No. 5,326,352 describes a variant of a prosthetic coupling device. The coupling device includes a first part and a second part, which are suitable to be connected together. The coupling device in accordance with its description differs substantially from the design in accordance with the present invention. For example, according to its description, the design requires tools to lock together and respectively release, the female member to or from the male member. The design excludes functionality when enclosed by cosmetics, because the locking member cannot be accessed without openings is the cosmetics.

A variant of an adjustable coupling device for a prosthesis is described in SE446373. The design consists of a so-called pyramid coupling. The pyramid coupling includes a first coupling part and at least one second coupling part. The design according to its description differs from the design in accordance with the present invention. For example, according to its description it does not allow disconnection without tools. The design excludes functionality when enclosed by cosmetics because the locking members cannot be accessed without openings in the cosmetics.

U.S. Pat. No. 6,981,992 describes a variant of an adaptor for connecting a sleeve to a coupling device included in a prosthetic leg. The coupling device in accordance with its description differs substantially from the design in accordance with the present invention. For example, according to its description, the design requires tools to lock together, respectively release, the female member to or from the male member. The design excludes functionality when enclosed by cosmetics because the locking members cannot be accessed without openings in the cosmetics.

A variant of a locking mechanism for a prosthesis is described in SE518263. The locking mechanism according to its description differs substantially from the design in accordance with the present invention. For example, the coupling of the prosthesis is accomplished with a completely different technology from that which is described in present invention. The design excludes functionality when enclosed by cosmetics because the locking members cannot be accessed without openings in the cosmetics.

A variant of a quick coupling for prostheses is described in U.S. Pat. No. 4,564,365. The design differs substantially from the design in accordance with the present invention. The design can hardly be enclosed in cosmetics without large openings to allow access to the releasing members. A realistic form of cosmetics is therefore not possible in a similar way as with the design in accordance with the present invention.

A variant of a coupling device for pipes is described in U.S. Pat. No. 5,435,604. The design can hardly be used to connect prosthetic parts that are enclosed in cosmetics. The coupling device requires large opening when connected to cosmetics to allow access to the releasing members. A realistic form of cosmetics is therefore not possible in a similar way as with the design in accordance with the present invention.

THE PURPOSE OF THE PRESENT INVENTION

The purpose of the present invention is to eliminate or substantially reduce at least one of the aforementioned or in the following description mentioned problems with existing types of coupling devices for prostheses. This purpose is accomplished with a coupling device in accordance with the present invention.

A BRIEF DESCRIPTION OF THE FIGURES

In the following detailed description of the present coupling device, references and references to the following figures will be made. Note that the figures are schematic and some parts of the coupling device may have been omitted, which are obvious to a professional in the technical field in which the coupling device is included.

FIGS. 1A and 1B schematically show a coupling device connected to a prosthesis and a user's leg.

DETAILED DESCRIPTION OF THE INVENTION

Figure 1A:
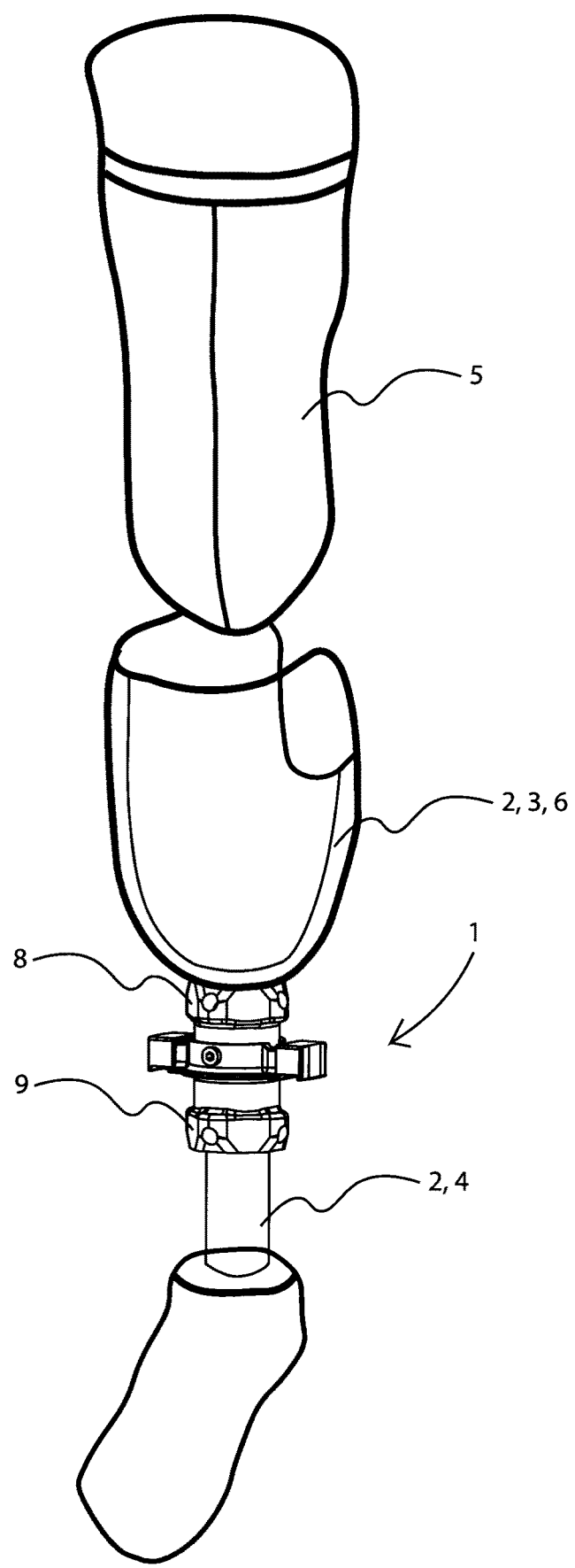

With reference to the figures, a coupling device 1 is here described in more detail. In the exemplifying embodiment, the coupling device 1 is used as a coupling device in a prosthesis 2 or similar. The coupling device 1 is preferably used to connect at least one first part 3 of a prosthesis 2 and at least one second part 4 of a prosthesis 2. Although the use of the coupling device 1 in applications in a prosthesis 2 is described in this patent application, this does not preclude the use of the coupling device 1 in other applications where the coupling device 1 is suitable for use. Furthermore, it is conceivable that the present invention is defined as a system, such as a prosthetic system, which includes at least one coupling device 1.

The first part 3 of the prosthesis 2 is suitable for connection to the remaining stump (limb, part) of an amputated extremity 5 in a human, directly or indirectly. In the exemplifying embodiment, the remaining part of the user's extremity 5 consists of a part of the user's legs and the prosthesis 2 mimics the amputated part of the leg such as a foot and part of the leg.

Figure 1B:
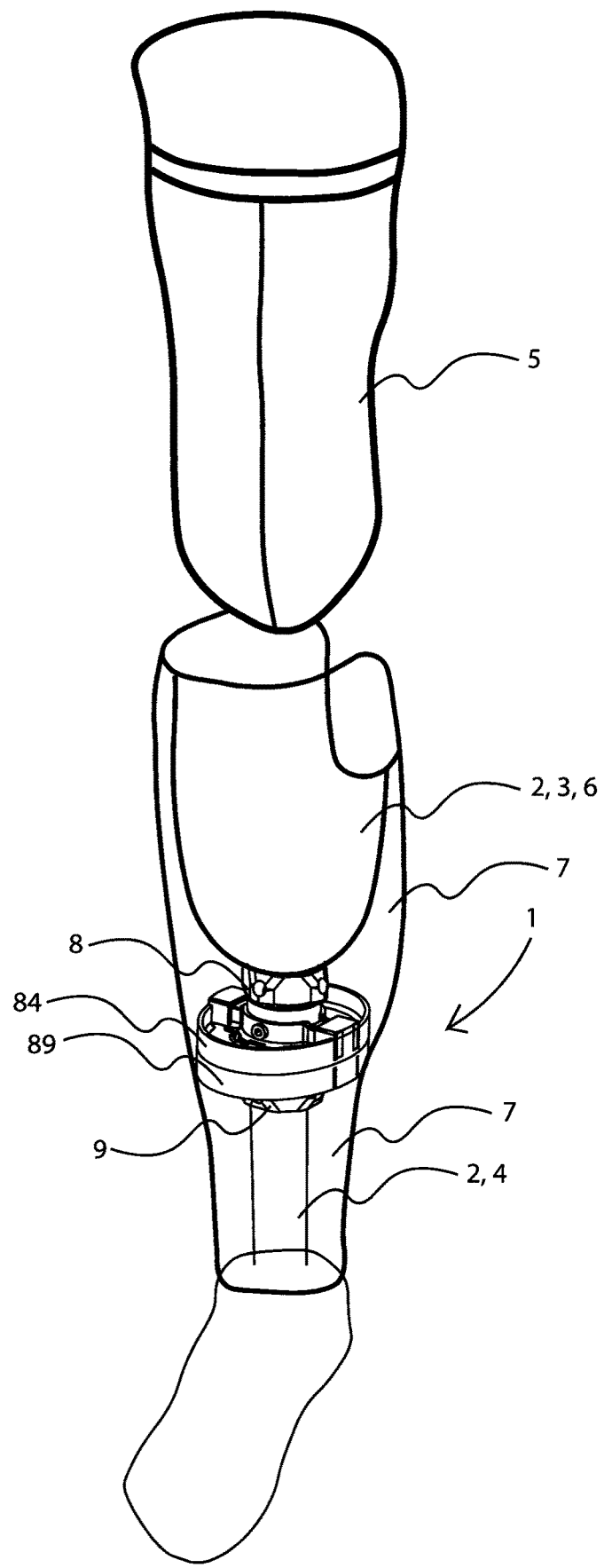
Figure 2A:
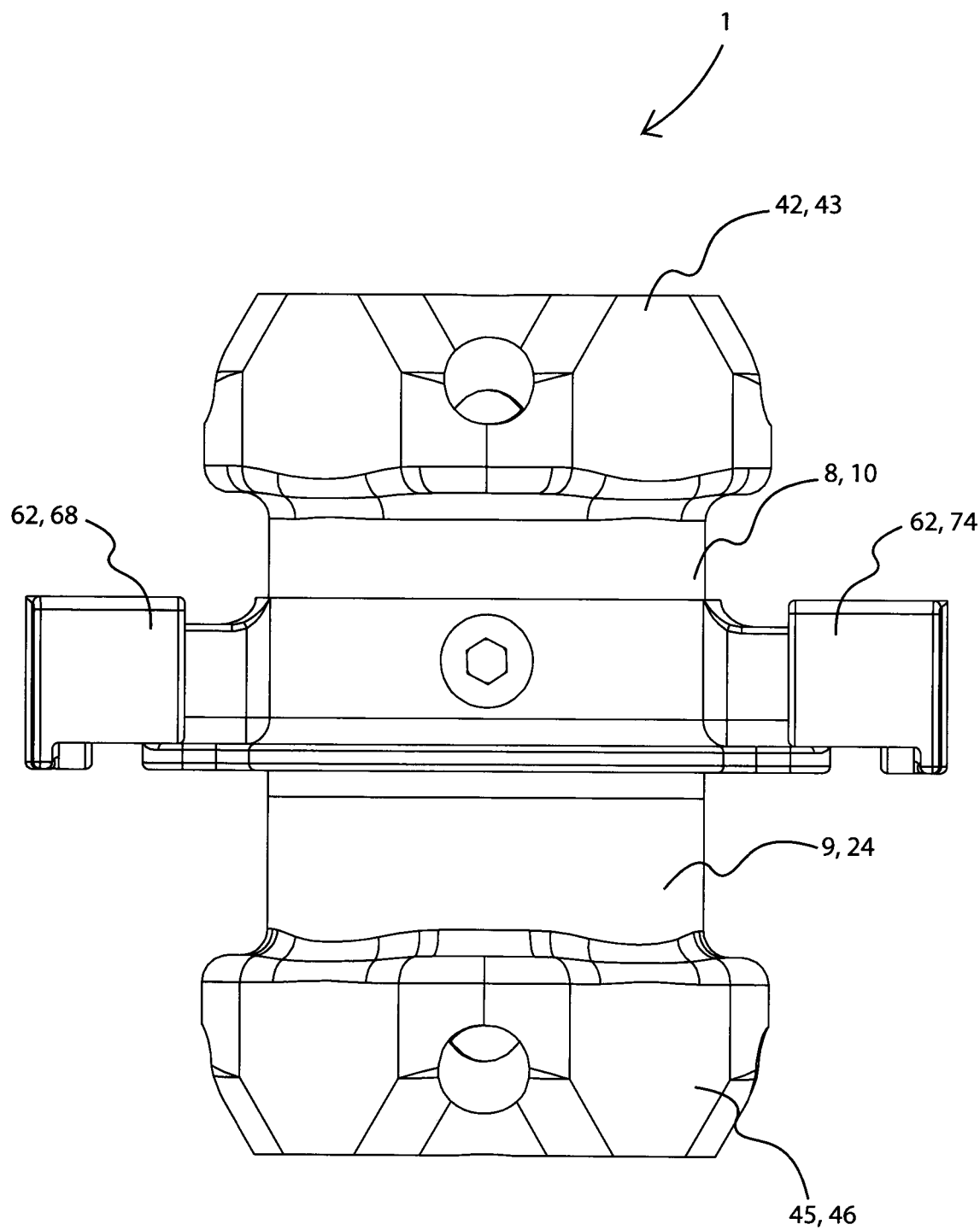
FIG. 2A shows a side view of the coupling device according to a first embodiment.
Figure 2B:
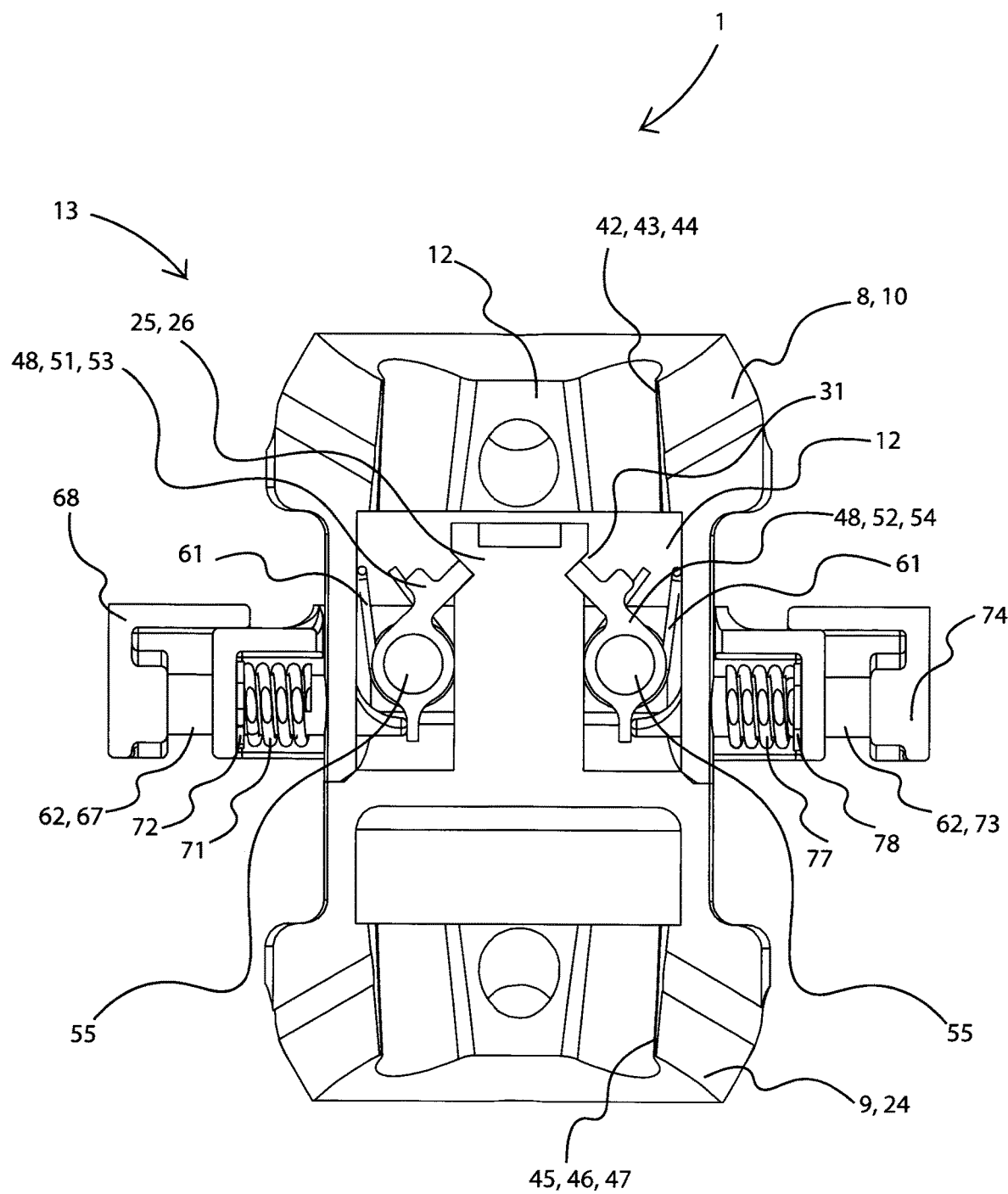
FIG. 2B shows a cross-sectional view of the coupling device according to the first embodiment.
Figure 2C:
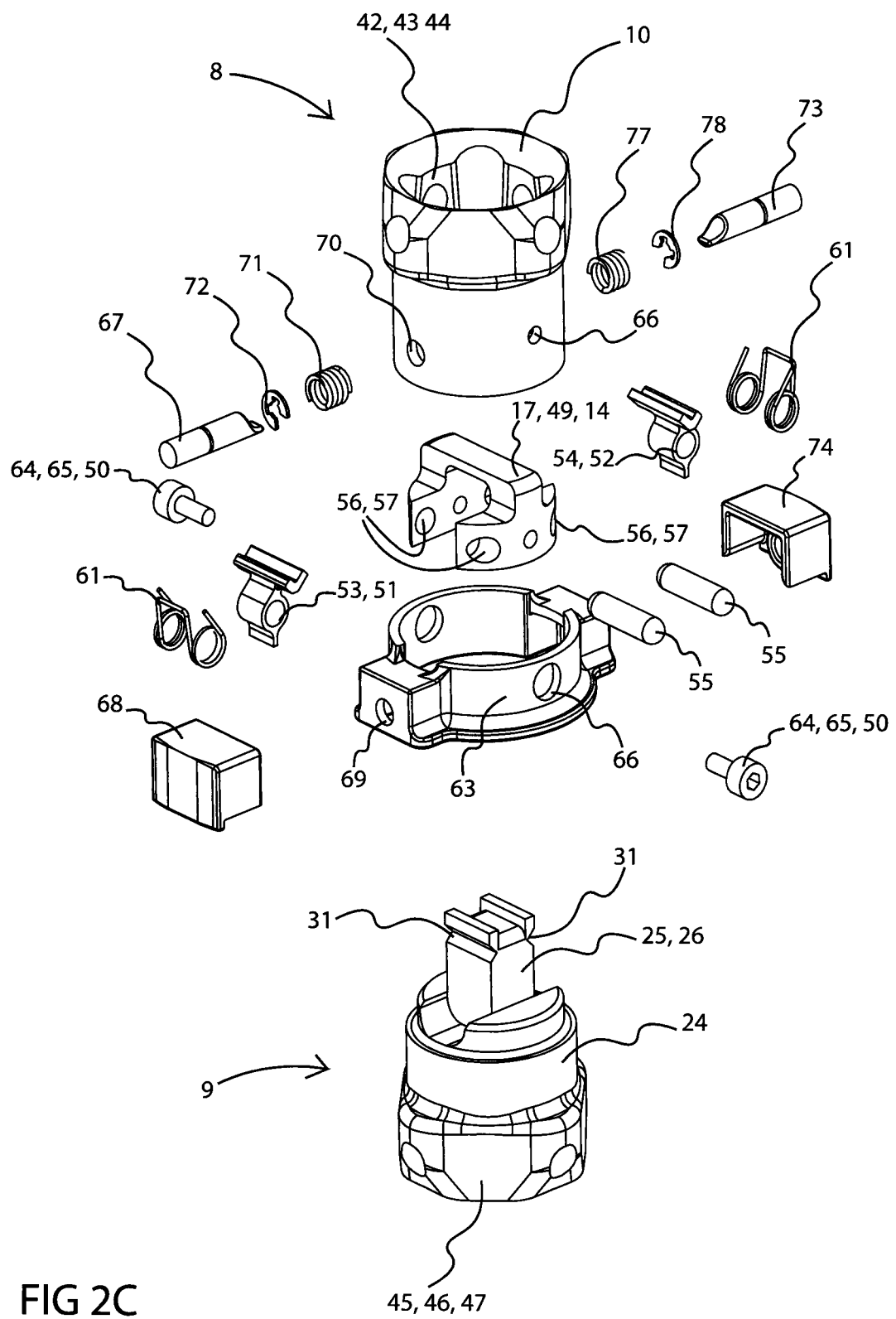
FIG. 2C shows an exploded view of the coupling device according to the first embodiment.
Figure 2D:
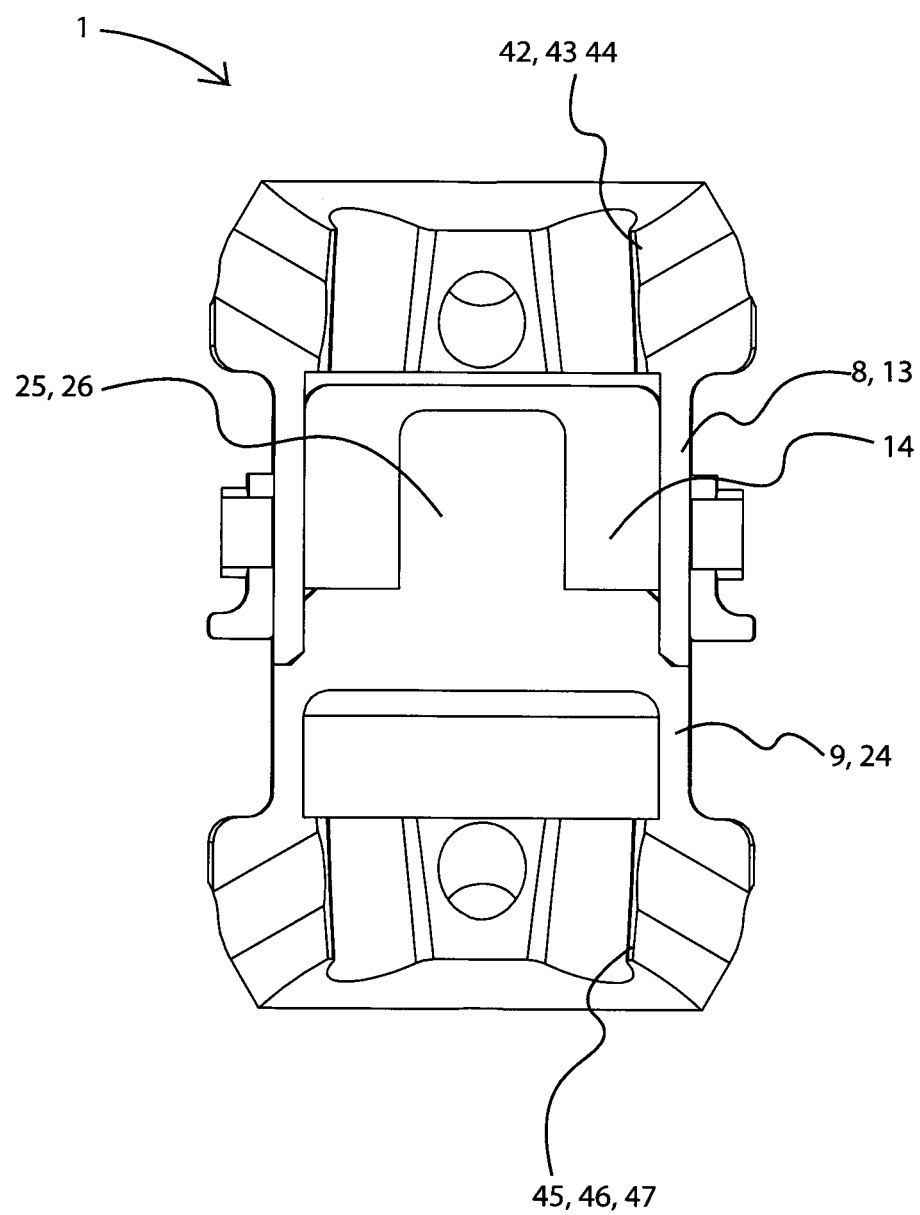
FIG. 2D shows a second cross-section of the coupling device.
Figure 3A:
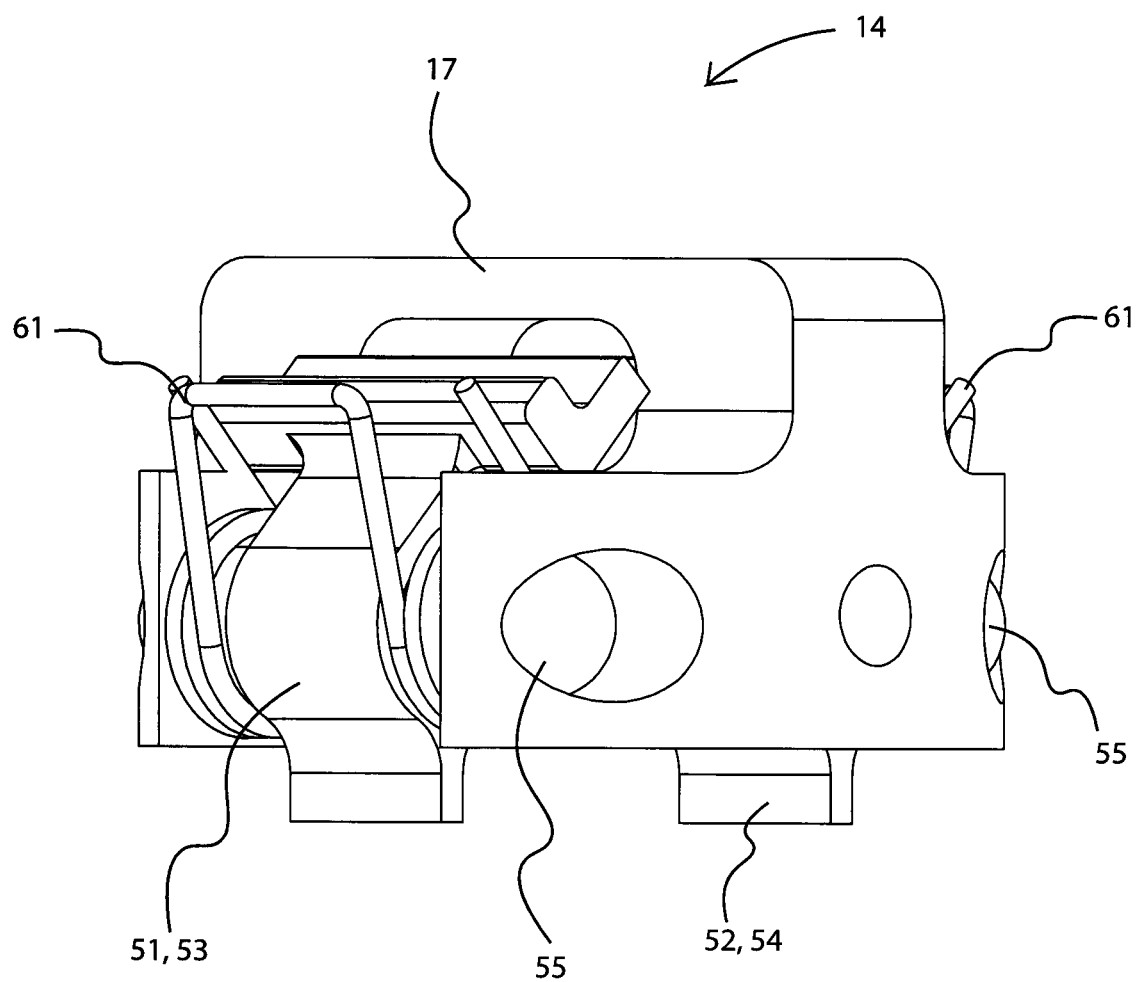
FIGS. 3A-3D show an exemplifying insert and an included bracket.
Figure 3D:
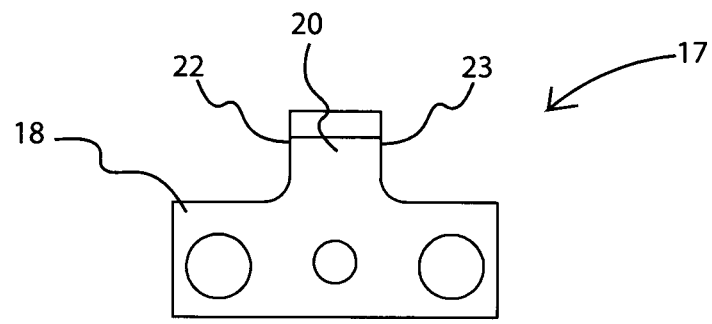
Figure 3C:
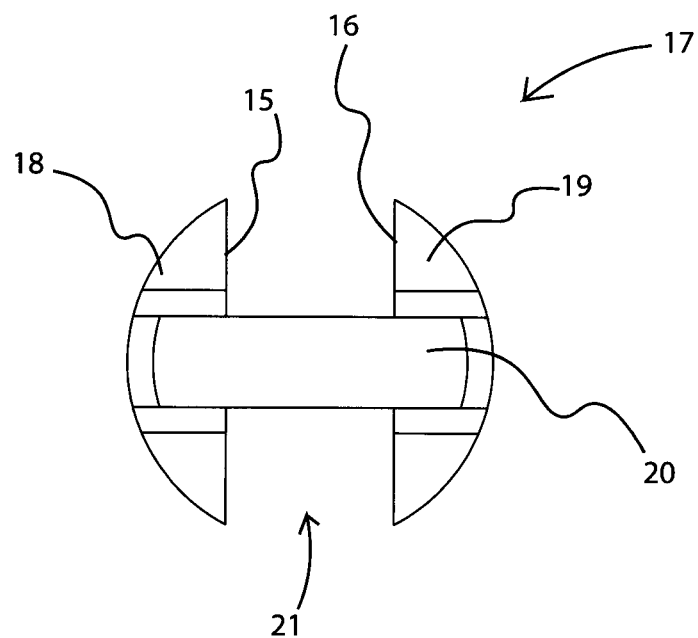
Figure 3B:
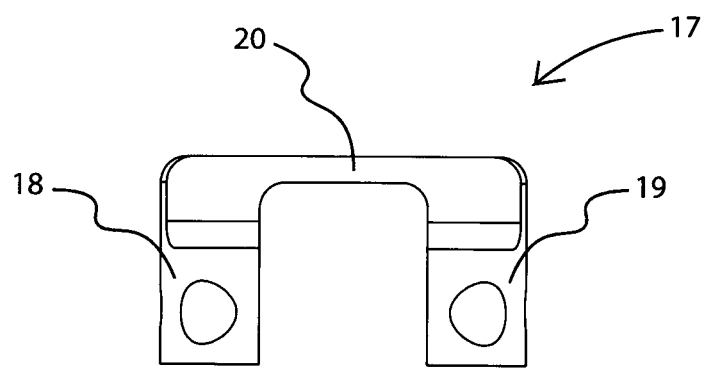

Preferably, the first part is 3 consists of the prosthesis 2, which is connected to the remaining part of the user's extremity 5, by at least one sleeve 6, attachment device or similar. The sleeve 6 consists of previously known technology in the prosthetic field, therefore it is not described in more detail in this patent application. FIG. 1B shows the use of the coupling device 1 in a prosthetic 2 with connected cosmetics (cosmetic cover) 7. At least one of the prostheses parts 3 and 4 is equipped with cosmetics 7 or suitable to be fitted with cosmetics. FIG. 1A shows the use of the coupling device 1 in a prosthesis without connected cosmetics 7. The cosmetics 7, for example, consists of foamed material which is enclosed by a silicone sock. The cosmetics 7 consists of some type of previously known technology, and therefore are not described in more detail in this patent application. For example, the cosmetics 7 can consist of a cover or similar of hard plastic or alternatively foamed material that is enclosed by, for example, silicone.

The coupling device 1 comprises at least one first coupling part 8 and at least one second coupling part 9. The coupling device's 1 first coupling part 8 and second coupling part 9 are designed so that they can be connected to each other and disconnected from each other. The specific feature of the present coupling device 1 is that the connection and disconnection of it can be accomplished without tools using just the hands. Connection and disconnection of the first coupling part 8 and the second coupling part 9 can occur even when the coupling device 1 is fully or partially enclosed in or surrounded by cosmetics (cosmetic cover).

The first coupling part 8 in the exemplifying embodiment comprises at least one first body 10, part, frame or similar. The first body 10 includes at least one first coupling member 11. The first body's 10 forms and dimensions can vary within the scope of the present invention. The body includes at least one hole 12, lead-through, in the axial direction of the body10. The hole 12 can consist of a bottom hole in the body 10 or be a through the body 10 lead-through hole.

In alternative embodiments, the shape of the hole's 12 cross-section can deviate from a round and/or cylindrical shape.

In the exemplifying embodiment, the first coupling member 11 consists of or includes at least one female member 13 or similar in the body 10. The female member 13 includes at least one hole, alternatively recess or a space. The female member 13 consists in its simplest form of the hole 12.

In the exemplifying embodiment, the female member 13 is completely or partially connected to, or integrated with, an insert 14. The insert 14 is attached to the second coupling part 9. The insert 14 is suitable for insertion and connection to the wall of the hole 12. Attachment is accomplished with at least one for the purpose previously known and suitable connector, such as screws, bolted joints or other suitable for the purpose connecting means. In a further embodiment, the insert is integrated with the first coupling part 8. The female member 13 consists in the exemplifying embodiment of part of the hole 12 and the space between two opposing parallel surfaces, a first surface 15 and a second surface 16, located at a distance from each other in the insert 14.

With reference to FIGS. 3A to 3D, a first embodiment of the insert 14 is shown. In the exemplifying embodiment, the insert includes at least one jumper-shaped part 17. In the exemplifying embodiment, the jumper-shaped part 17 includes at least one first mounting part (fastener) 18 and at least one second mounting part (fastener) 19 and at least one third mounting part (intermediate mounting part) 20. In the exemplifying embodiment, the first mounting part 18 and the second mounting part 19 have a cross-section that is radius-shaped against the wall of the hole 12. In one of the axial ends of the mounting parts 18 and 19, the intermediate mounting part 20, or the attachment part, is connected to the mounting parts 18 and 19. A gap 21 is created between the first surface 15 and the second surface 16. The intermediate mounting part 20 includes at least one first steering surface 22 and at least one second steering surface 23. In alternative embodiments, the jumper-shaped part 17 can be of another suitable for the purpose design and shape.

The second coupling part 9 comprises at least one second body 24, part, frame or similar. The second body's 24 shape (form) can vary within the scope of the present invention. The second body 24 includes at least one second coupling member 25. In the exemplifying embodiment, the second coupling member 25 consists of or includes, a protruding male member 26, peg (dowel) or similar. The second coupling member 25 therefore consists of a coupling member which can also be termed as male, male member or similar. The protruding male member is in its exemplifying embodiment directed in the axial direction of the coupling part 9. The male member 26 is suitable for connection to the female member 13.

Figure 4B:
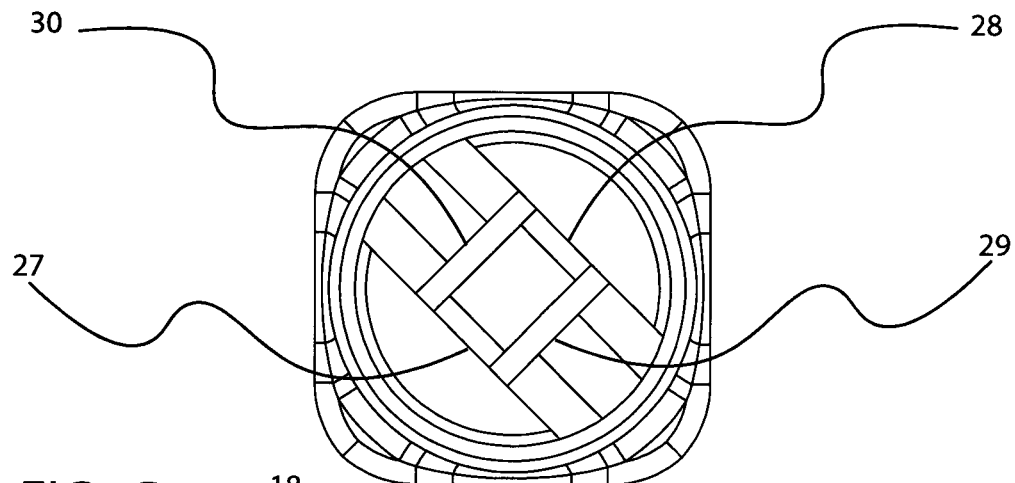
FIGS. 4A and 4B show a male member in more detail from the side and from above.
Figure 4A:
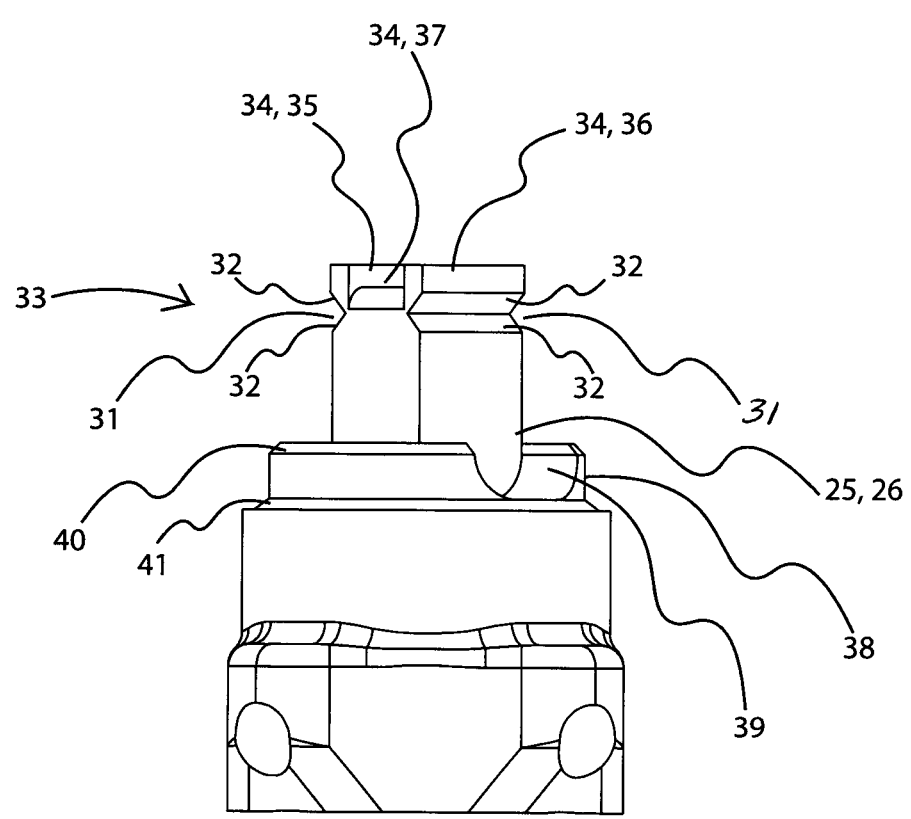
Figure 5:
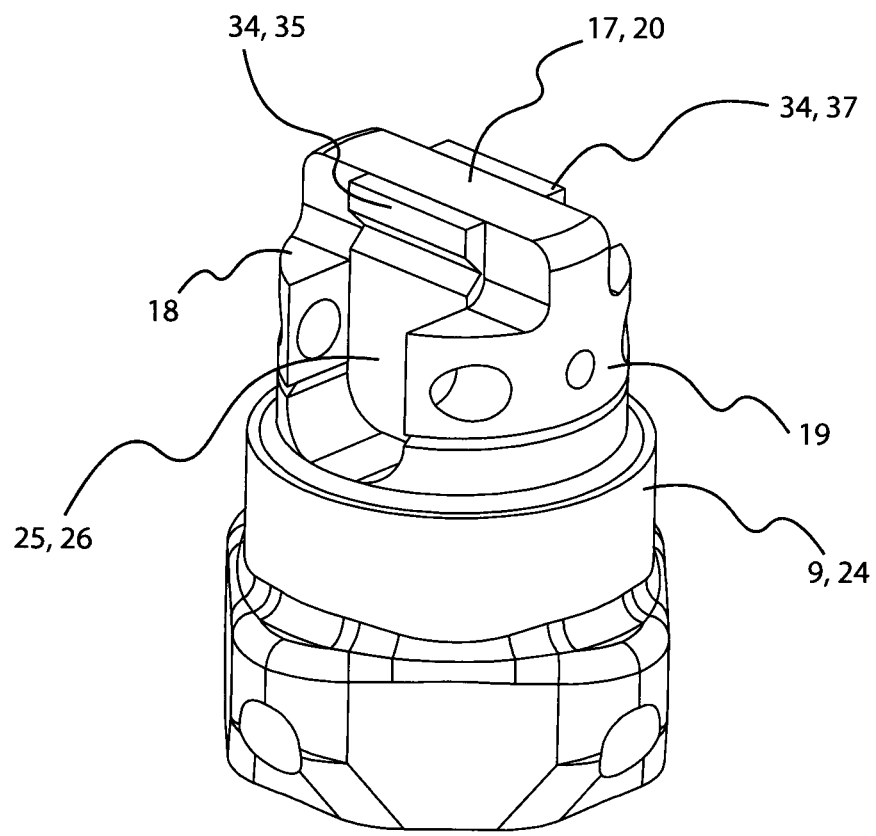
FIG. 5 shows interconnected male and female members with certain exclusions.

With reference to FIGS. 4A and 4B, a first embodiment of the male member is shown in more detail. The shape and the dimensions of the protruding male member 26, peg can vary within the scope of the present invention. The male member 26, peg, has in its exemplifying embodiment a square cross-section, or essentially a square cross-section. In alternative embodiments, the shape of the cross-section of the male member 26 can deviate from a square cross-section. The quadrangular cross-section in the exemplifying embodiment is square. Each respective corner can include a bevel, radius, or similar. The male member 26, peg, includes a first side 27 with a first opposite side 28 and a second side 29 with a second opposite side 30. The first side 27 and the first opposite side 28, or alternatively the second side 29 and the second opposite side 30, are suitable during connection to rest against the female member's 13 first surface 15, edge, and the female member's second surface 16, edge. The first surface 15 and second surface 16 are parallel or essentially parallel and positioned at a distance between each other. The dimensions of the male member 26, peg, that is to say, the distance between the first surface 27 and the opposite surface 28 and the distance between the second surface 29 and the second opposite surface 30 are adjusted after the distance between the first surface 15 of the female member and the second surface 16 of the female member. The male member's 26, peg's, length is further adjusted after the length of the first surface 15 of the female member 13 and after the length of the second surface 16 of the female member 13, in the axial direction of the coupling part 8.

The protruding male member 26 includes at least one track 31, groove, bevel, notch or similar. The track includes locking surfaces 32. In the exemplifying embodiment the male member 26 includes at least one first track 31 and at least one second track 31. The tracks 31 are placed on two opposing sides of the male member's 26 peg, such as for example the peg's 26 first side 27 and the peg's 26 first opposite side 28, alternatively the peg's 26 second side 29 and the peg's 26 second opposing side 30. The track 31, or alternatively the tracks 31 are in the embodiment V-shaped. However, this does not preclude that track 31, or tracks 31, has or have another for the purpose suitable form (shape). The angle of the V-shaped tracks (grooves, notches) 31 can vary within the scope of the invention.

Again with reference to FIG. 4A, the male member 26 at its free end 33 is shown including at least one steering device 34, positioning (guiding) device, which during connection of the first coupling member 11, the female member 13, with the second coupling member 25, the male member 26, is suitable to steer their mutual positions. The steering device 34 includes at least one first steering edge 35, at least one second steering edge 36, and one intermediate track 37, groove notch or the like. The design also includes at least one third steering edge 38 and at least one first recess 39. The design also includes at least one first bevel 40 and at least one second bevel 41.

For example, the cross-section of the male member 26 can have more or fewer edges than four. The cross-section of the male member 26 can also be of a non-circular form such as an elliptical cross-section. It is essential that the first coupling member 11 and the second coupling member 25 each have cross-sections that allow the interconnection of the first coupling member 11 and the second coupling member 25 and that play or similar is essentially minimized or eliminated.

The first coupling part 8 includes at its other end an attachment device 42 which is suitable for connection to the sleeve 6 or to another attachment device connected to the user's extremity. In the exemplifying embodiment, the attachment device 42 consists of a first pyramid coupler 43. The pyramid coupler 43 consists of a previously known design and is therefore not described in more detail. The first pyramid coupler 43 includes a female part 44 and a male part (not shown in figures). One of these, the female part or the male part, is connected to the sleeve and the other is connected to the coupling part. In the exemplifying embodiment, the male part is connected to the sleeve 6. The first pyramid coupler's 43 female part 44 is in its exemplifying embodiment integrated with the body 10. In alternative embodiments, the attachment device is a separate part which is attached to the body 10 of the first coupling part 8. In alternative embodiments the attachment device 42 consists of another design suitable for the purpose. The pyramid coupler's 43 male and female part are screwed together with stop screws or similar, not shown in the figures.

The second coupling part 9 includes, at its other end, a second attachment device 45 which is suitable for connection to the prosthesis 3 or to another attachment device connected to the user's extremity. In the exemplifying embodiment, the second attachment device 45 consists of a second pyramid coupler 46. The second pyramid coupling 46 consists of a previously known design and is therefore not described in more detail. The second pyramid coupler 46 includes a female part 47 and male part (not shown in figures). One of the female or male parts is connected to the prosthesis and the other of the female or male part is connected to the second coupling part 9. In the exemplifying embodiment, the male part is connected to the prosthesis 3. The female part 47 of the attachment device 45 is in its exemplifying embodiment integrated with the insert. In alternative embodiments, the attachment device 45 consists of another for the purpose suitable attachment device.

The design, shape and dimensions of the male member 26 and the female member 13 are in the interconnected position suitable for reducing the risk of mutual movement between the male member 26 and the female member 13 and thereby reduce the risk of the occurrence of play between the male member 26 and the female member 13. In order to reduce play between the female member's 13 and the male member's 26 connection surfaces, contact surfaces (mating surfaces) or the like, their tolerances provide a suitable play for the purpose, and are mutually appropriate.

When connecting the first coupling part's 8 first coupling member 11 and the second coupling part's 9 second coupling member 25, the male member 26 is inserted into the female member 13. To lock together the first coupling part's 8 first coupling member 11 with the second coupling part's 9 second coupling member 25, the coupling device 1 includes at least one locking device 48, or alternatively a securing (latching) device or similar. The locking device 48 includes at least one bracket 49, attachment device or similar with which the locking device 48 is connected to the first coupling part 8. The bracket 49 is attached to the second coupling part with at least one fastener 50 such as at least one screw, screw joint or other suitable fastener. The connection of the bracket 49 to the first coupling part 8 can also be accomplished by gluing or similar. For free-form production (3d printing) of the coupling part 8, the bracket 49 is preferably integrated with the first coupling part 8. The screw can be connected to at least one hole. The exemplifying locking device 48 includes at least one first locking member 51 and at least one second locking member 52. The locking device's 48 first locking member 51 and second locking member 52 are suitable to lock the first coupling part 8 to the second coupling part 9. Preferably, the locking of the first locking member 51 and the second locking member 52 is temporary. However, this does not preclude the first locking member 51 and the second locking member 52 being connected more permanently to each other.

In the exemplifying embodiment, the first locking member 51 consists of at least one first flap 53, or similar. In the exemplifying embodiment, the locking device 48 includes at least one first flap 53 and at least one second flap 54. The respective first flap 53 and second flap 54 are pivotally arranged around the axis of rotation in an axle 55, peg or similar, to which each respective flap is connected. The axles 55 are each connected to an attachment member 56 in the bracket 49. In the exemplifying embodiment, the attachment member 56 consists of holes 57 in the bracket 49 or insert 14. Each flap 53 and 54 is connected to each axle 55 via a through hole 58. The flaps 53 and 54 are pivotally arranged between a first position, constituting a locked position for the coupling parts 8 and 9, and at least one second position, constituting an unlocked position for the coupling parts 8 and 9.

Figure 6A:
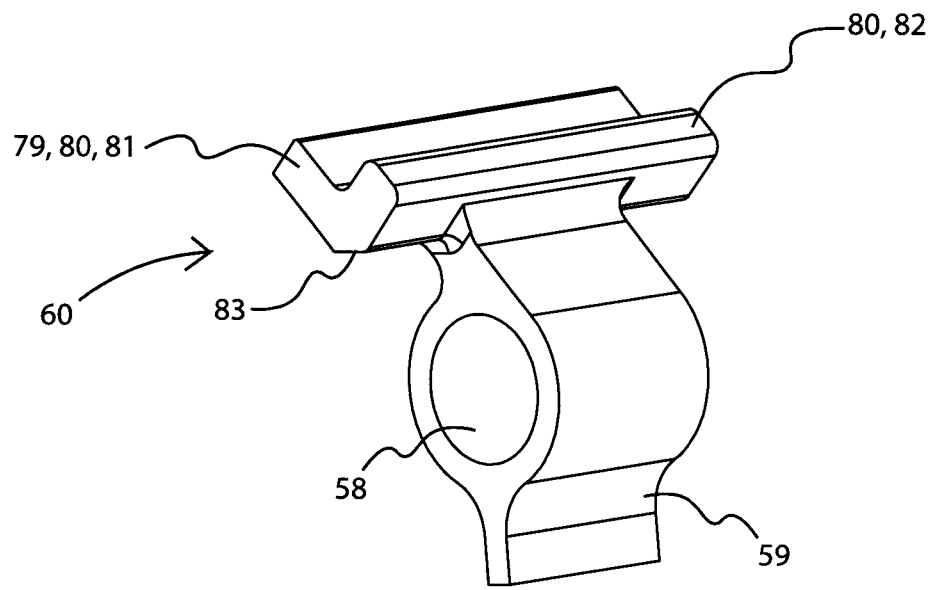
FIGS. 6A and 6B show an exemplifying flap.
Figure 6B:
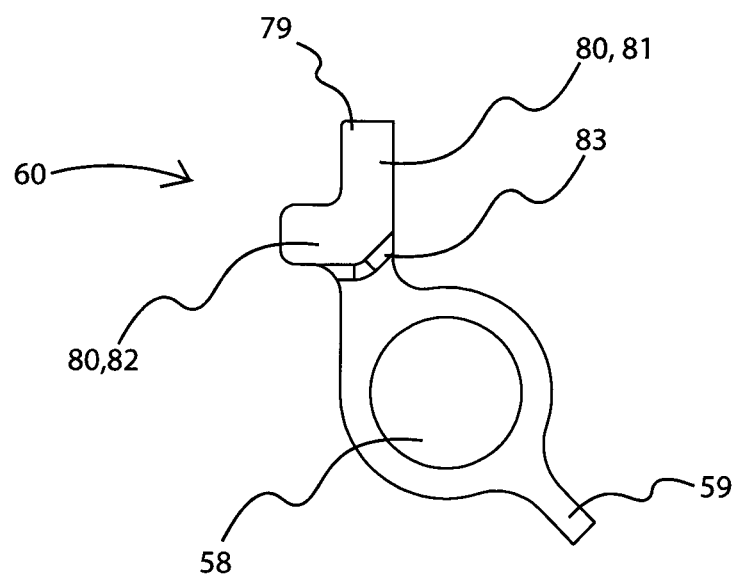
Figure 7A:
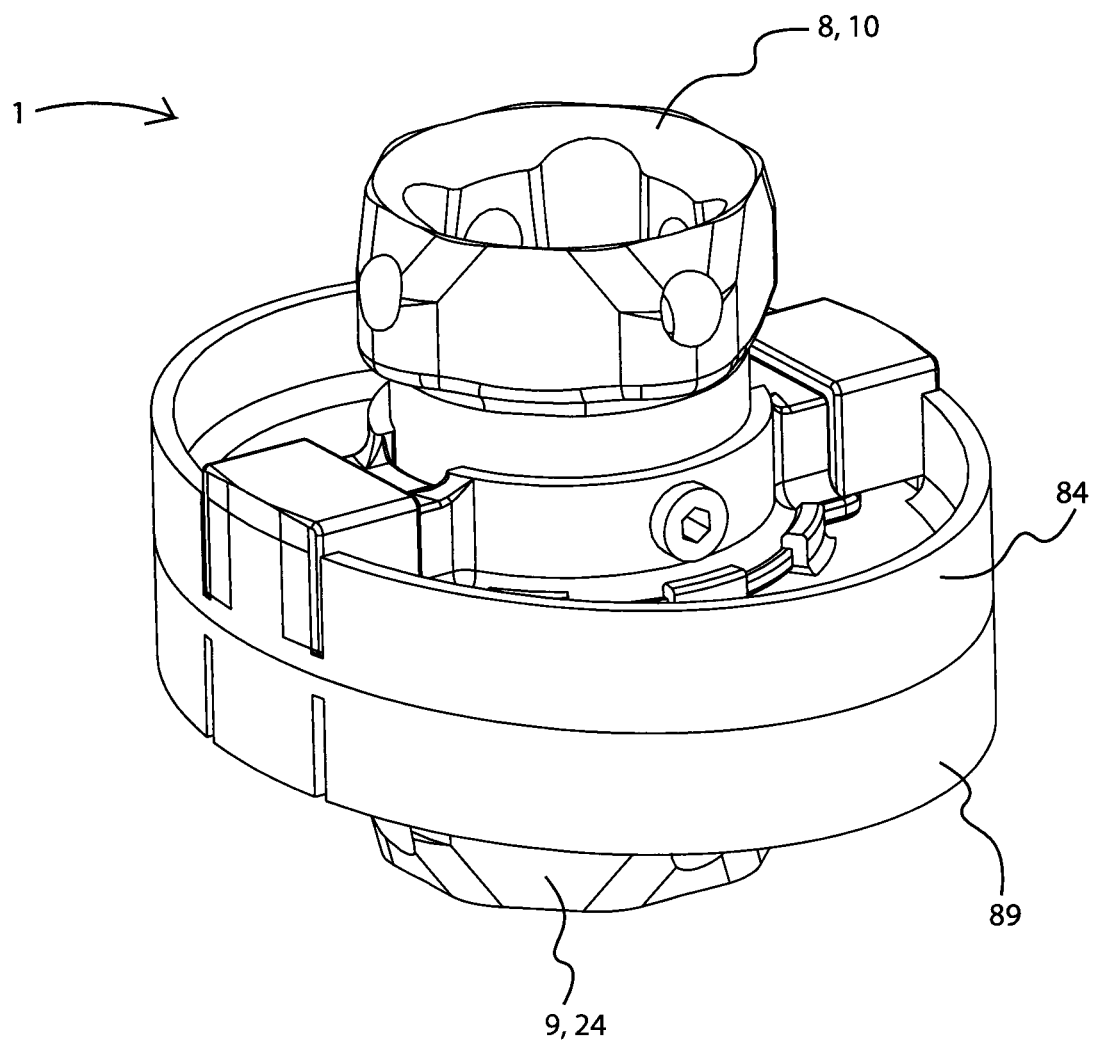
FIG. 7A shows the coupling device in accordance with a second embodiment.
Figure 7B:
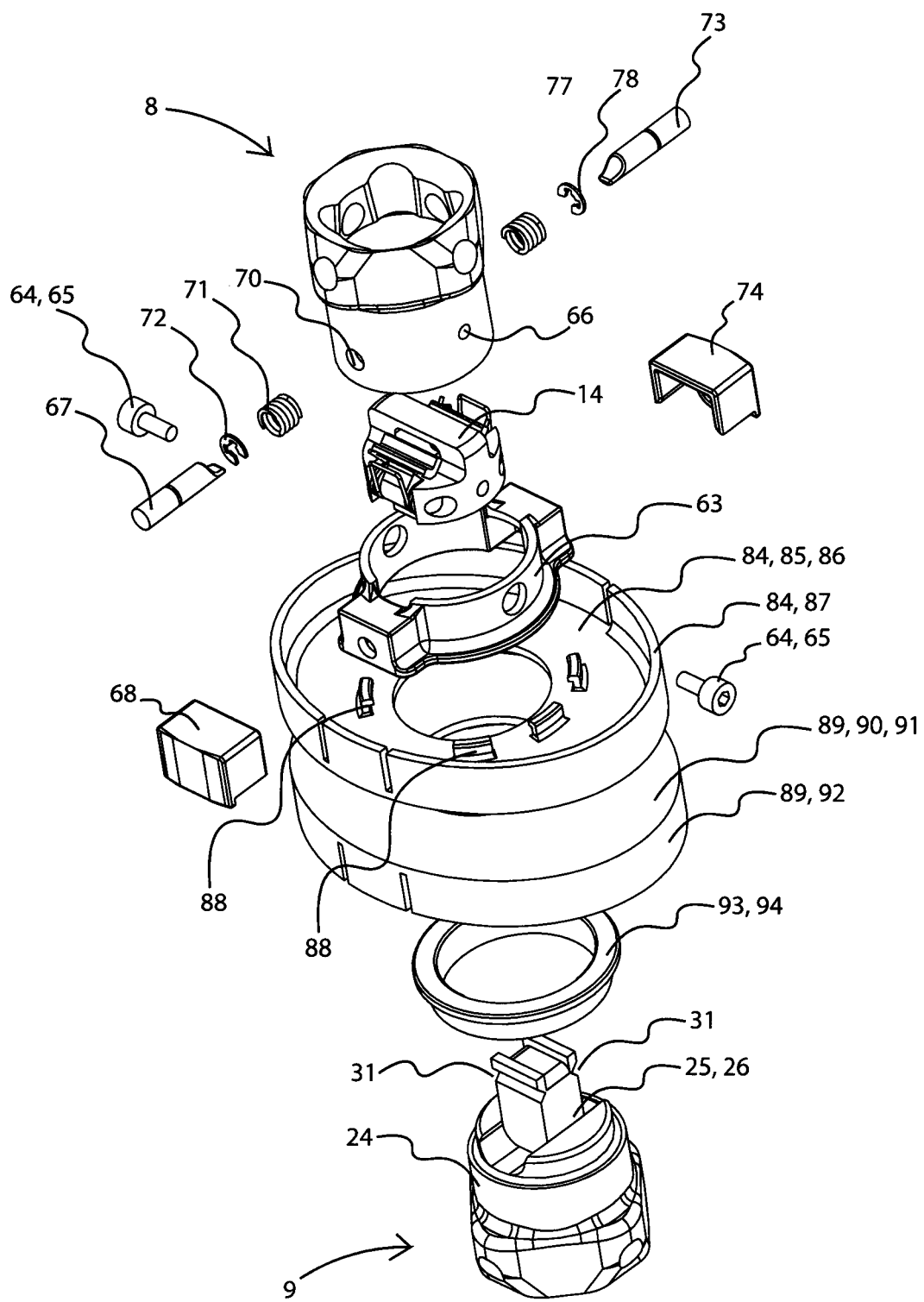
FIG. 7B shows an exploded view of the coupling device according to the second embodiment.

With reference to FIGS. 6A and 6B, an exemplifying flap 53 and 54 are shown in more detail. The flaps 53 and 54 each include at least one first flap part 59 and at least one second flap part 60. The flaps 53 and 54 are each spring loaded via at least one spring 61 or similar.

In the exemplifying embodiment, the spring 61 consists of a torsion spring. In alternative embodiments the spring 61 can be of another for the purpose suitable type of spring. Each flap 53 and flap 54 is affected by at least one spring 61 to be pivoted towards the male member. Each flap 53 and 54 goes into each track 31 of the male member.

The design comprises at least one disengaging device 62 with which the locking device 48 can be actuated so that the first coupling part 8 and the second coupling part 9 are released from each other. The disengaging device 62 includes at least one bracket 63. The bracket 63 is connected to the body 10. The connection of the bracket 63 to the body 10 can be done via at least one fastener 64, which for example consists of at least one screw 65 which connects to at least one hole 66 in the body 10. In the exemplifying embodiment, the disengaging device 62 is made up of at least one, in the radial direction, displaceable (slidable) first disengagement member 67, which is operated with at least one first maneuvering member 68. The disengagement member 67 is pivotally arranged via a first hole 69 in the bracket 63 and a second hole 70 in the body 10. The disengagement member 67 is spring loaded via at least one first spring 71 and includes a first locking member 72 which prevents the disengagement member 67 from unintentionally disengaging from the body 10 through the hole 69 by way of the spring force.

In the exemplifying embodiment, the disengagement member 67 also includes at least one in the radial direction displaceable (slidable) second disengagement member 73 which is operated with at least one second maneuvering member 74. The second disengagement member 73 is pivotally arranged in relation to the bracket 63. The second disengagement member 73 is pivotally arranged via a first second hole 75 in the bracket 63 and a second second hole 76 in the body 10. The second disengagement member 73 is spring loaded via at least one second spring 77 and includes at least one second locking member 78 which prevents the second disengagement member 73 from unintentionally disengaging from the body 10 through the hole 75.

Referring to FIGS. 6A and 6B, a first embodiment of the flap 53 and the flap 54 is shown.

The second flap part 60 includes a locking member 79, which is suitable to engage with the track 31 of the male member 26. In the exemplifying embodiment, the locking member 79 is part of an angular part 80. In the exemplifying embodiment, the locking member 79 consists of the first part 81 in the angular part 80. The second part 82 of the angular part 80 is a support for the spring 61. The angular part 80 includes at least one pivot limiting part, surface, 83 which limits the maximum pivot of the flap 53 and/or the flap 54 so that it is not swung too far in relation to the axial center of the female part.

Respectively, the first flap 53 and the second flap 54 are affected by the respective spring 61 to pivot towards the male member 26 so that a temporary locking with the tracks 31 occurs when the male member 26 is inserted in the female member 13. When the male member 26 is inserted into the female member 13, the first flap 53 and the second flap 54 are affected by the male member 26 to be swung out from the center of the female member 13, resulting in the respective spring 61 being tightened. When the flaps 53 and 54 and locking member 79 reach the position of each respective track 31, the first flap 53 and the second flap 54 of each respective spring 61 are affected to be swung into the groove 31, resulting in the first coupling part 8 and the second coupling part 9 being locked with each other.

The first disengagement member 67 affects the first flap's 53 first flap part 54 to pivot around the axis of rotation in the axle which in turn causes the second flap's 54 second flap part 55 to be swung from its engagement with the track 31 in the male member. The second disengagement member 73 affects the second flap's 54 first flap part 59 to be pivoted around the axis of rotation in the axle 55 which in turn causes the second flap part 60 to be swung out from its engagement with the track 31 of the male member 26. Both the disengagement members 67 and 73 must be engaged in order to release the first coupling part 8 and the second coupling part 9. If only one of the disengagement members 67 or 73 is engaged, the first coupling part 8 is not released from the second coupling part 9. It is not sufficient, therefore, that only one of the first disengagement member 67 or the second disengagement member 73 be maneuvered.

In the exemplifying embodiment, the first coupling part 8 includes at least one first holder 84, alternatively cover, bracket or attachment device for cosmetics (cosmetic cover) 7. The cosmetics are connected to the first holder 84. Alternatively, the holder 84 is integrated with the cosmetics. The first holder 84 for cosmetics 7 consists of a tray-shaped part 85. The tray-shaped part 85 includes at least one plate 86 with a rim 87. The holder 84 for cosmetics is connected to the bracket 63 for the locking device 48. In the exemplifying embodiment, attachment is accomplished by quick release brackets 88. In alternative embodiments, attachment is done with other suitable technology.

In the exemplifying embodiment, the second coupling part 9 includes at least one second holder 89, alternatively cover, bracket or attachment device for cosmetics 7. The cosmetics are connected to the first holder 84. Alternatively, the holder 84 is integrated with the cosmetics. In the embodiment, the second holder 89 for cosmetics 7 consists of a second tray-shaped part 90. The second tray-shaped part 90 includes at least one second plate 91 and at least one second rim 92. The second holder 89 for the cosmetics 7 is connected to the second coupling part 9. The design includes at least one bracket 93 for the 89 holder, which consists of a ring-shaped member 94. In the exemplifying embodiment, attachment is accomplished by quick release brackets. In alternative embodiments, attachment is done with other suitable technology.

Figure 8:
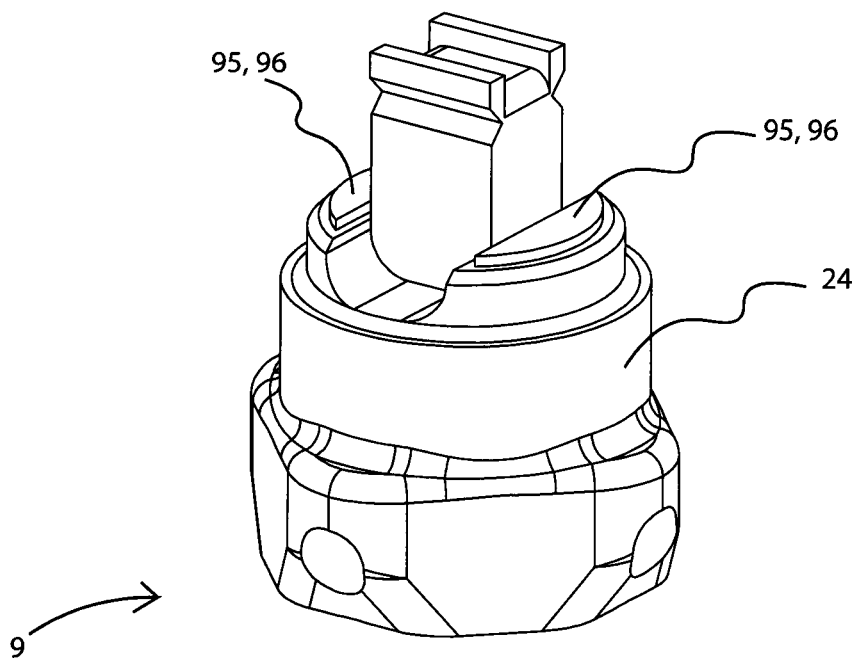
FIG. 8 shows a dampening device in more detail.

With reference to FIG. 8, an alternative embodiment of the present coupling device 1 is shown, where it includes at least one dampening device 95. The dampening device 95 can also be seen as a pretension device. In the exemplifying embodiment, the damping device consists of at least one dampening material layer 96. The dampening material layer 96 consists of a material suitable for the purpose. The dampening material layer 96 is located between the surfaces of the male member 26 and the female member 13, insert or bracket.

Figure 10:
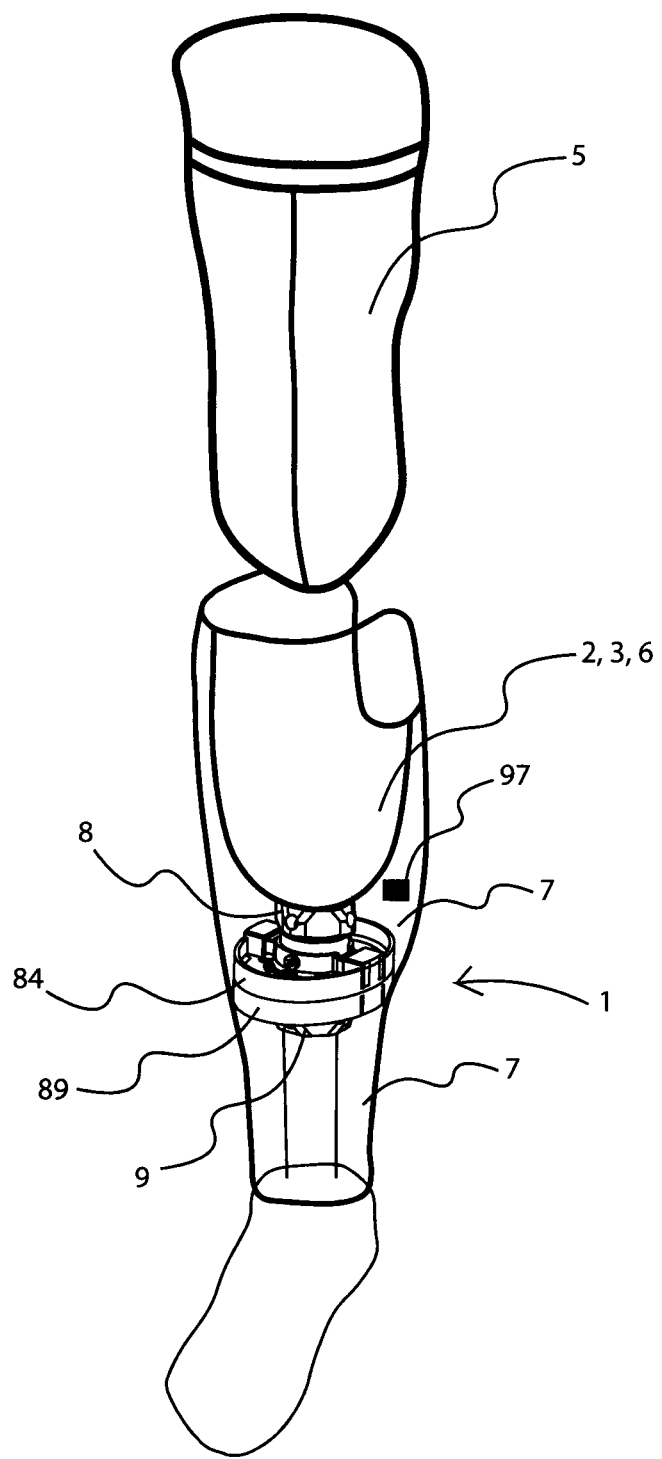
FIG. 10 shows an additional embodiment of the coupling device.

With reference to FIG. 10, an alternative embodiment is shown in which the cosmetics are connected to the first holder 84, alternatively the cover, bracket or attachment device for cosmetics and the second holder 89, alternatively cover, bracket or attachment device for cosmetics. In the alternative embodiment at least one accumulator 97, for supply of electrical energy to a function in the prosthesis, is connected or integrated with the cosmetics 7. Electrical wiring connects the accumulator and the electrically operated unit in the prosthesis. The required wiring is connected to the accumulator. To enable disconnection of the first coupling part and the second coupling part, the coupling parts include connectors for connecting electrical wiring in the various prosthetic parts.

Figure 9A:
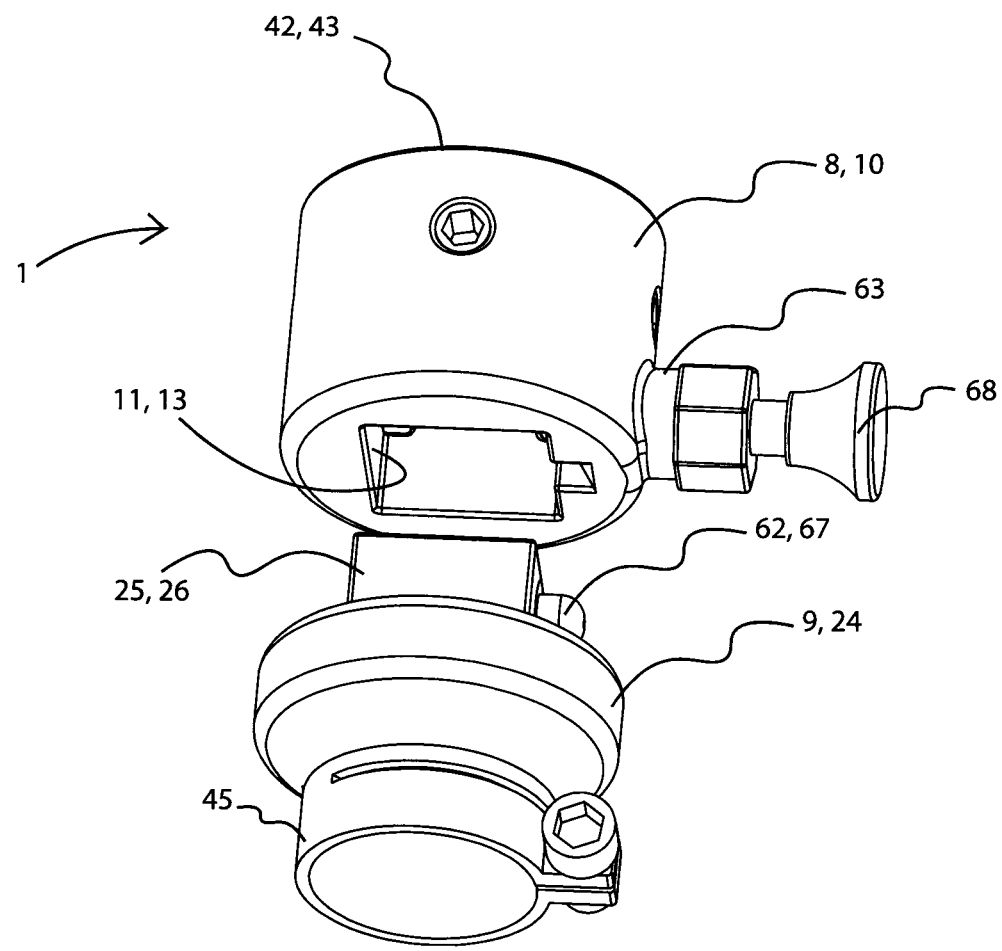
FIGS. 9A-9C show an alternative embodiment of the invention.
Figure 9B:
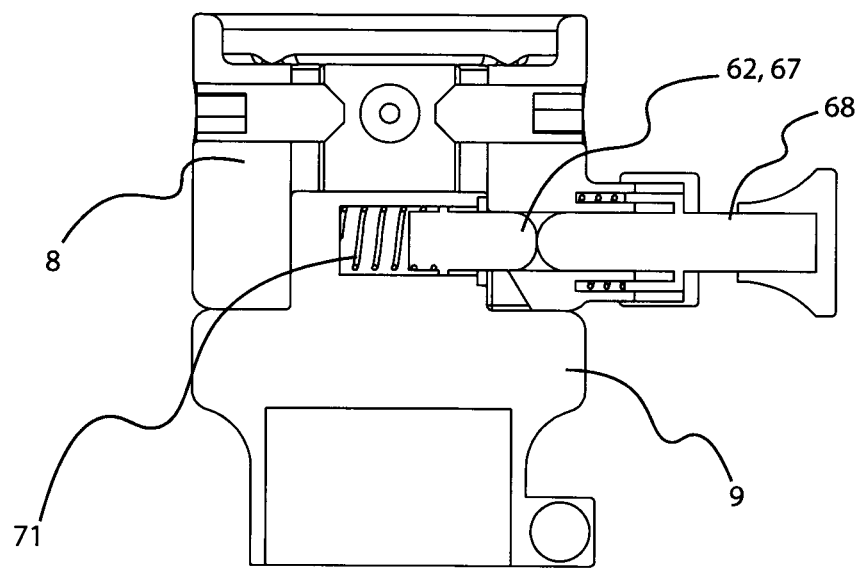
Figure 9C:
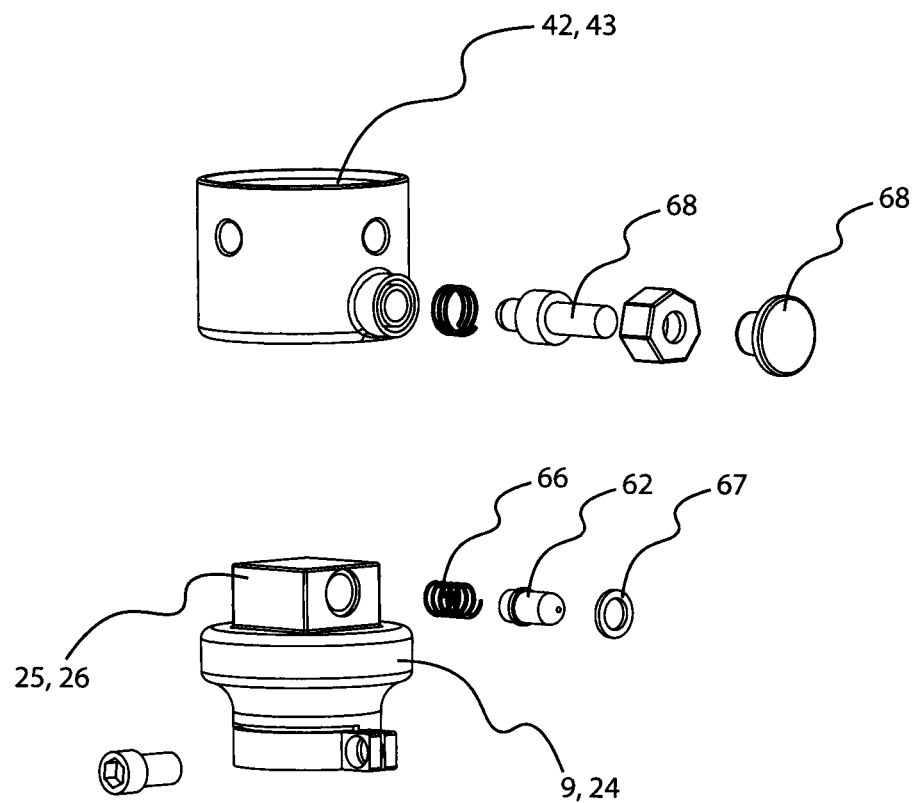

With reference to FIGS. 9A to 9C, an alternative embodiment of the coupling device 1 is shown. In this alternate embodiment, the coupling device includes 1 at least one first coupling part 8, and at least one second coupling part 9. The first coupling part 8 includes a first coupling member 11. The second coupling part 9 includes at least one second coupling member 25. The first coupling member 11 consists of one female member 13 and the second coupling member 25 consists of a male member 26. In the exemplifying embodiment, the female member 13 consists of a hole with a square or rectangular cross-section. In the embodiment, the male member 26 consists of a pin (peg, dowel) with a square or rectangular cross-section. The design includes at least one locking device 48 and at least one disengaging device 62.

Figure 11A:
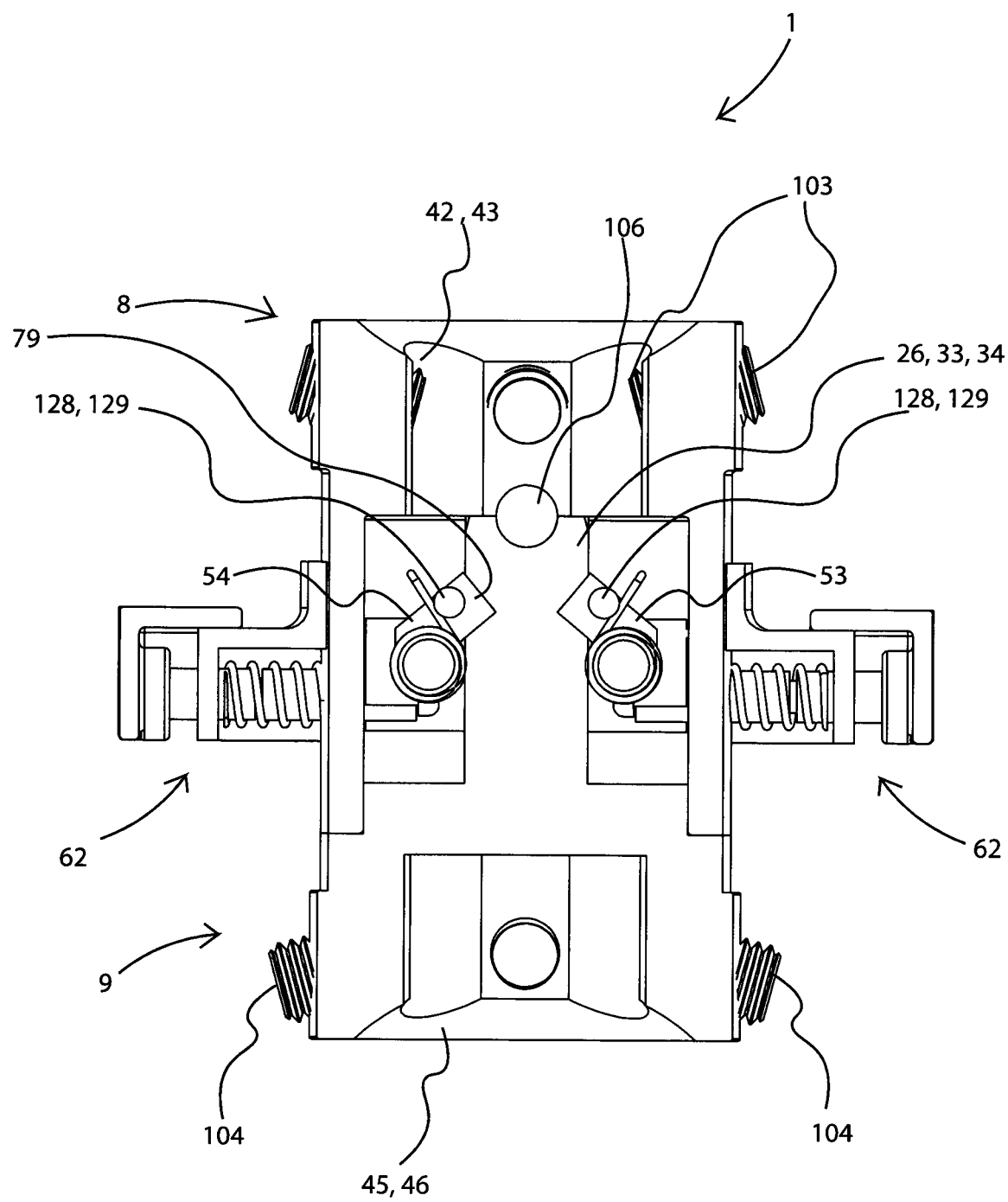
FIG. 11A shows an alternative embodiment of the coupling device in a cross-section.
Figure 11B:
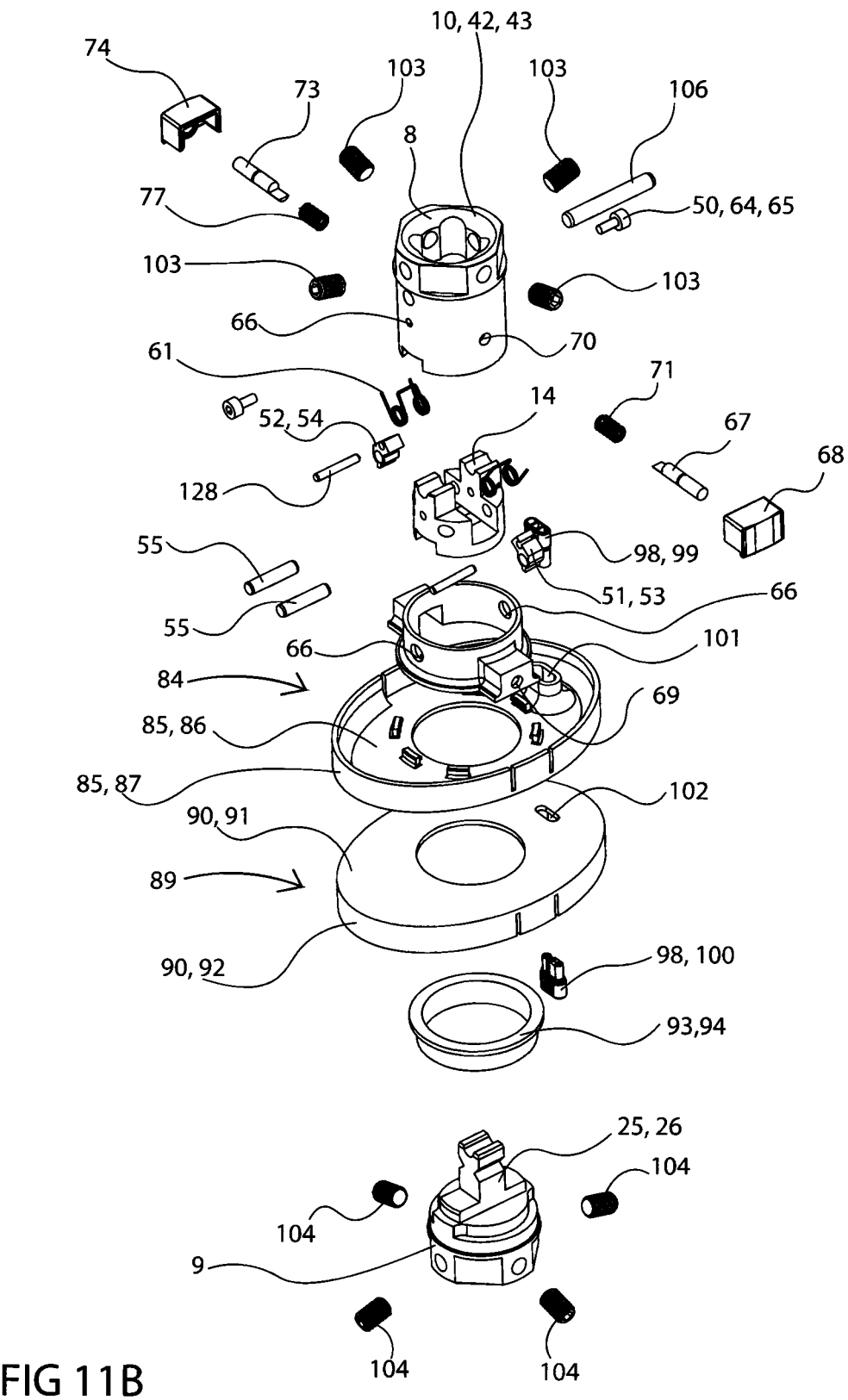
FIG. 11B shows an exploded view of the second alternative embodiment.

With reference to FIGS. 11A and 11B, an alternative embodiment of the present coupling device 1 is shown. In FIG. 11A, the alternative embodiment of the coupling device 1 is shown in a cross-section in which the holders 84 and 89, alternatively cover, a bracket or attachment device for cosmetics 7 are omitted. This does not preclude, however, that the alternative embodiment of the coupling device 1, as shown in FIG. 11A, can include holders 84 and 89, alternatively covers, brackets or attachment devices for cosmetics. In FIG. 11B, the alternative embodiment of the coupling device 1 is shown in an exploded view that includes the exemplifying embodiments of holders 84 and 89 for cosmetics 7. The design details, positions, which are alike in the second embodiment which are described in the first embodiment are not further detailed but referenced to the description of the first embodiment.

In the alternative embodiment of the coupling device 1 shown in the exploded view in FIG. 11B, the coupling device includes 1 at least one connector 98. The exemplified connector 98 includes at least one first connector part 99 and at least one second connector part 100 which can be connected and disconnected. The first connector part 99 is connected to the first holder 84 via a bracket 101, hole, through hole or the like. The second connector part 100 is connected to the second holder 89 via a second bracket 102, hole, through hole or the like. In FIGS. 11A and 11B, screws 103 or similar are shown in the first pyramid coupling 43 and screws 104 or similar are shown in the second pyramid coupling 46. The design of the pyramid coupling is of the previously known type, which is not described in more detail.

In the alternative embodiment of the coupling device 1, it includes at least one first coupling part 8 and at least one second coupling part 9. The coupling device's 1 first coupling part 8 and second coupling part 9 are designed so that they can be connected to each other and disconnected from each other without the need for special tools or gear (this does not preclude that a muscle weak users may need some type of tool or aid to help connect or disconnect the coupling device). This applies specifically when cosmetics are connected to the first coupling part 8 and the second coupling part 9. The purpose of the alternative embodiment of the coupling device 1 is to further reduce the occurrence of play between the constituent components of the coupling device 1, when the first coupling part 8 and the second coupling part 9 are connected to each other. Reduced play is achieved by modifications of the coupling device's 1 constituent components such as preferably modifications of the first coupling part 8, the second coupling part 9, insert 14 and the locking members 51 and 52 as well as the flaps 53 and 54 which is described in more detail in the following with reference to FIGS. 12 to 15. The coupling part 8, insert 14 and the second coupling part 9 include linking (interlocking, mating) shapes that steer them mutually so that play between said components is reduced to a substantial minimum.

Figure 12A:
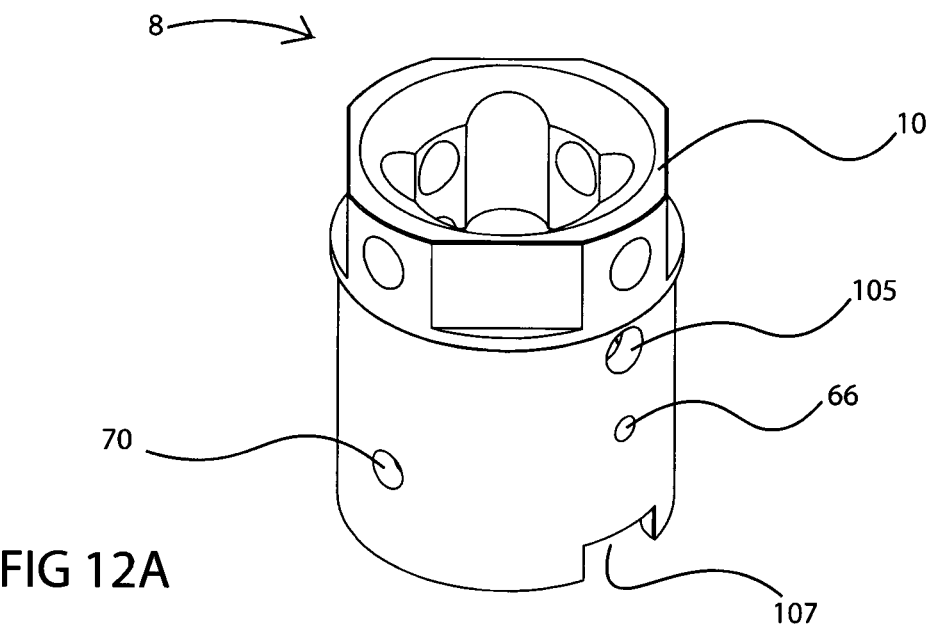
FIGS. 12A and 12B show an alternative embodiment of the first connecting part.
Figure 12B:
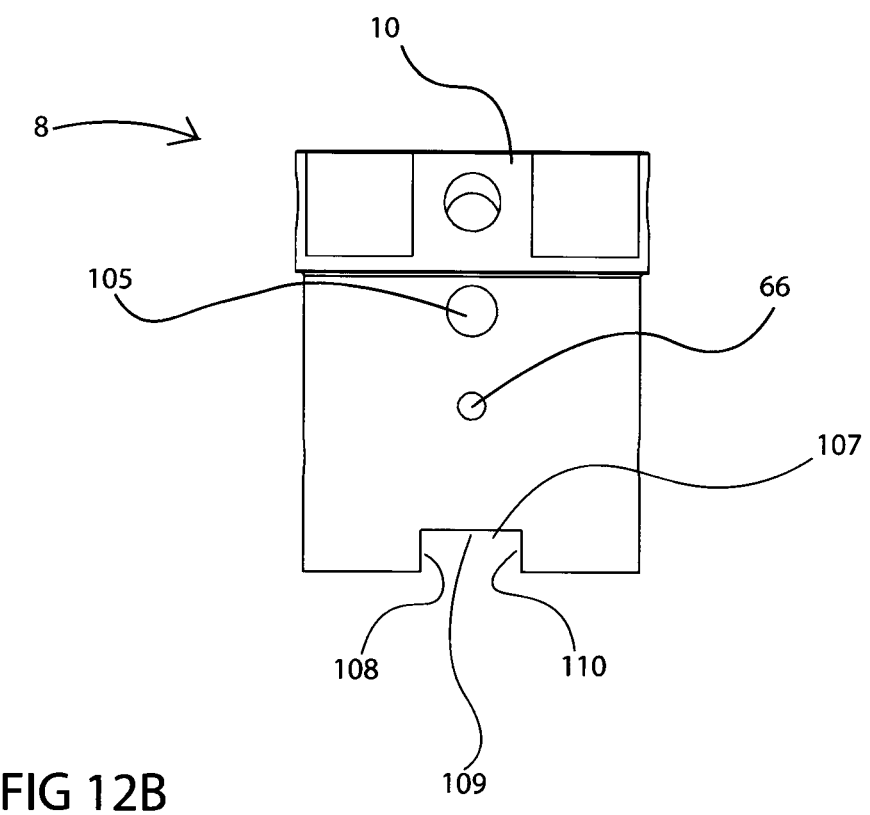

With reference to FIGS. 12A and 12B, an alternative embodiment of the first coupling part 8 is shown. The first coupling part 8 includes at least one first body 10 comprising at least one first coupling member 11. In the alternative embodiment, the first coupling part's 8 body 10 includes at least one hole 105 and at least one opposing hole, not shown in figures, for at least one guide pin 106, shown in FIGS. 11A and 11B. The guide pin 106 is inserted through the hole 105 through the inner space and into the opposing hole. The guide pin is transverse to the second coupling part 8. The guide pin's 106 and the hole's function are to control the insert's 14 position in relation to the coupling part's 8 steering device 34, located at the free end 33 of the male member 26. The second coupling part 9 includes at the opposite end, i.e. the end comprising the female part of the pyramid coupling, at least one first recess 107 and at least one second recess 107. The first recess 107 and the second recess 107 are mutually opposing.

The recess 107 includes a third steering surface 108, a fourth steering surface 109 and a fifth steering surface 110 which are steering surfaces, contact surfaces, in relation to the second coupling part's 9 male member 26.

Figure 13A:
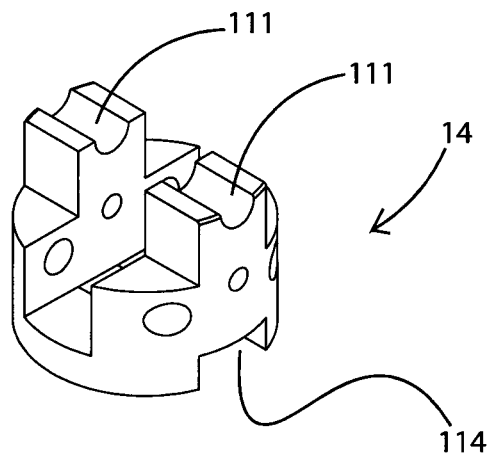
FIGS. 13A-13C show an alternative embodiment of the second connecting part.
Figure 13B:
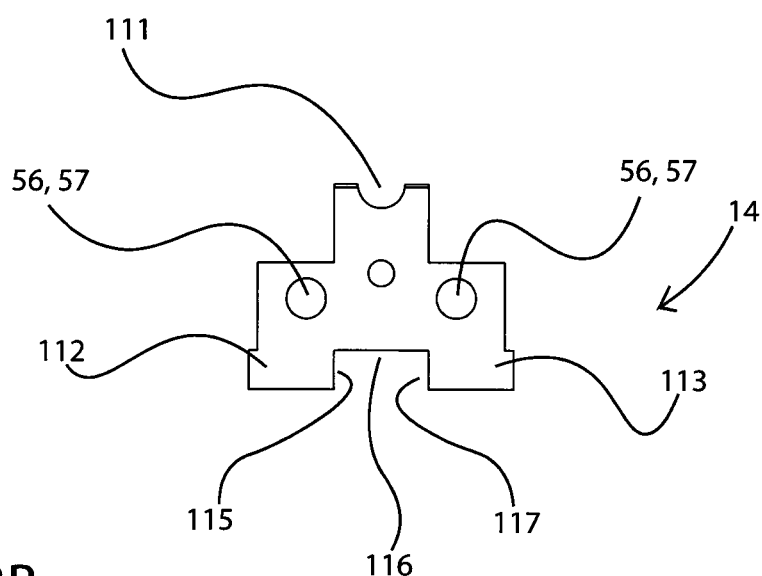
Figure 13C:
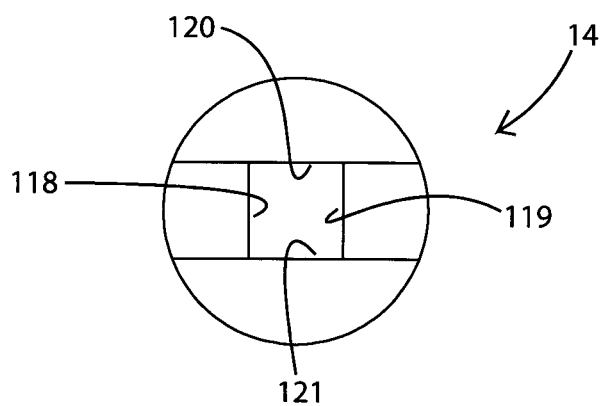

FIG. 13 shows an alternative embodiment of the insert 14. In the alternative embodiment of the insert 14, the third mounting part 20 is not present in accordance with the insert in accordance with the first embodiment. The function achieved by the first mounting part 18 in the first embodiment of the insert 14 is achieved in the second embodiment of the aforementioned guide pin 106 and recesses 111 in the insert 14. The guide pin 106 is not integrated with the mounting part according to the first embodiment. The guide pin 106 consists of a component that can be assembled and disassembled. The guide pin 106 replaces the transverse intermediate mounting part 20 in the first embodiment of the insert 14. The guide pin 106 preferably has a round cross-section. The first mounting part (fastener) 18 and the second mounting part (fastener) 19 of the insert 14 include at each of their free ends at least one of the aforementioned recesses 111. The recess 111, recesses 111, consist preferably of a radius-shaped recess or a convex recess. The axial direction of the first recess 111 in the first mounting part (fastener) 18 and the axial direction of the recess 111 in the second mounting part (fastener) 19 coincide or essentially coincide with each other. The first mounting part (fastener) and the second mounting part (fastener) are held together by at least one joining part 112, preferably at least one first joining part 112 and at least one second joining part 113.

The insert 14 includes at least one third recess 114 or similar. In the exemplifying embodiment, the insert comprises at least one first third recess 114 and at least one second third recess. The third recess 114 includes at least one sixth steering surface 115, at least one seventh steering surface 116 and at least one eighth steering surface 117.

In the embodiment, the insert forms a female member comprised of a square hole with at least one first side 118, at least one opposite side 119, at least a second side 120 and at least one second opposite side 121. To the square hole, constituting the female member of the embodiment, the male member 26 of the second coupling part is suitable to be connected. The female member has preferably a square cross-section, but this does not preclude that the female member can have a different form (shape) of its cross-section than square.

Figure 14A:
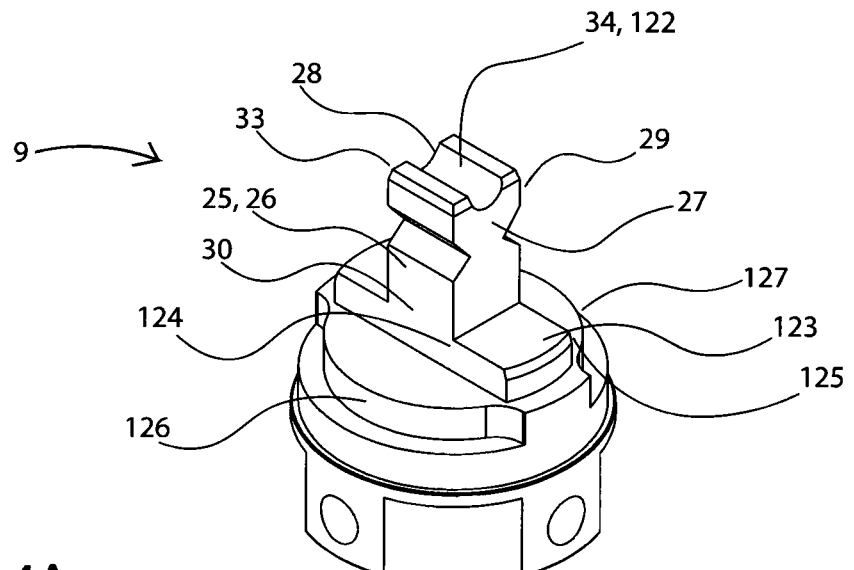
FIGS. 14A and 14B show an alternative embodiment of the insert.
Figure 14B:
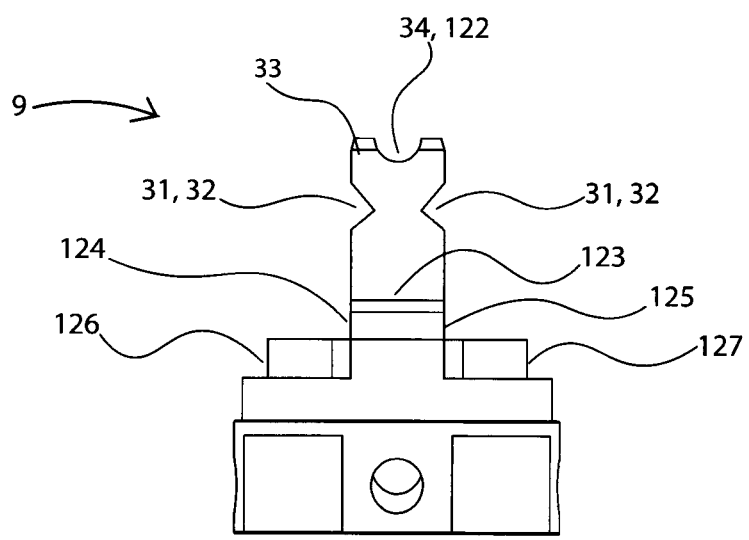

With reference to FIGS. 14A and 14B, an alternative embodiment of the second coupling part 9 is shown. The second coupling part 9 includes at least one male member 26 suitable for connection to the female member in the second coupling part and insert 14. In the embodiment shown in FIG. 14, the male member 26 at its free end 33 includes at least one steering device 34 which, when connecting the male member 26 to the female member 13, guides the mutual positions between the female member 13 and the male member 26. The steering device 34 at the free end 33 consists in the exemplifying embodiment of a fourth recess 122 (equivalent to an intermediate track 37 in the first embodiment) extending from side 27 of the male member 26 to the opposite side 28 of the male member 26. The recess 122 preferably has a radial shape, which interacts with the guide pin's 106 shape and radius. The said radial shape of the recess 122 and the guide pin's shape 106 can be of another for the purpose suitable shape (form) other than a radial shape.

With reference to FIG. 14, it is shown that the male member includes steering surfaces, guiding parts, which further positions the first coupling part 8, the insert 14 and the second coupling part 9 mutually to each other. In the exemplifying embodiment, reduced play is achieved between the first coupling part 8 and the second coupling part 9, among other things, by the second coupling part's male member 26 including at least one segment 123 or guiding surface, which extends a stretch in a direction from the male member in the radial direction. Further, the 123 segment, guiding surface, has an extension in the axial direction of the male member 26. The segment 123 includes at least one fourth guide edge 124 or guiding surface and at least one fifth guide edge 125 or guiding surface which are steered in relation to the recess 114, surfaces 115 and 117 or similar in the insert 14 and to the surfaces 108 and 109 in the first coupling part 8.

The second coupling part also includes at least one ninth guiding surface 126 and at least one tenth guiding surface 127, which steers the second coupling part 9 in relation to the first coupling part 8. The said guiding surfaces and the forms (shapes) of the recesses can vary within the scope of the present invention.

Figure 15A:
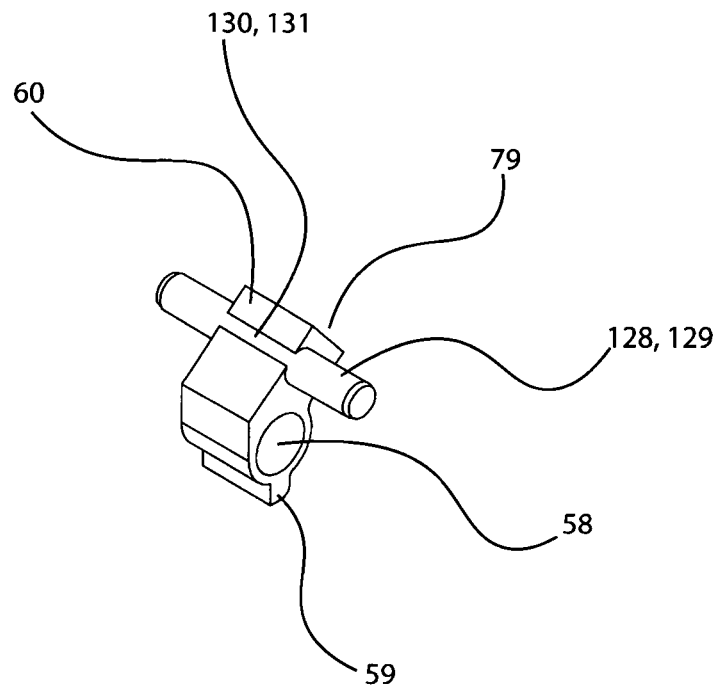
FIGS. 15A and 15B show an alternative embodiment of the flaps.
Figure 15B:
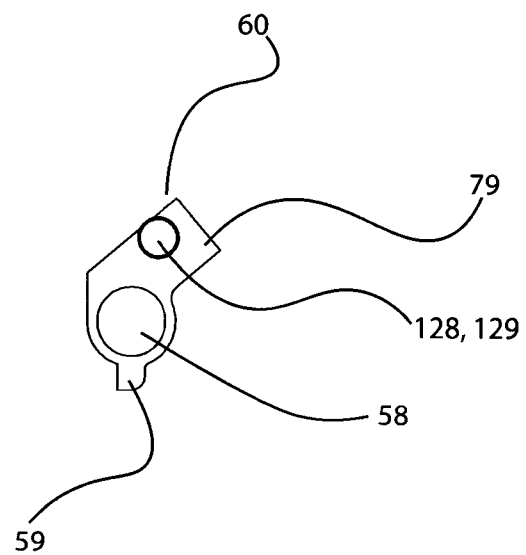

FIG. 15 shows an alternative embodiment of the first flap 53 and the second flap 54. In the exemplifying embodiment, the first flap 53 and the second flap 54 are identical or essentially identical. In the exemplifying alternative embodiment, the flaps 53 and 54 include at least one locking member 79 which, when connecting the female member and the male member engage with the V-shaped track 31 of the male member. The track 31 of the male member is adapted to the locking member's 79 form (shape). Each respective flap 53 and 54 also includes a spring support 128, which, in the exemplifying embodiment, consists of a rod 129 with a round cross-section, which is attached to a hole in the flap 53 or flap 54. In the exemplifying embodiment of flap 53 alternatively flap 54, each respective flap 53 and 54 includes at least one slit 130 that extends in the axial direction of the hole, which allows the hole 131 being dimensioned so that a springy-effect, locking, between the material around the hole and the rod is achieved.

Each flap's 53, 54 design, according to the alternative embodiment, has the advantage that it reduces the cost of manufacturing the flap 53, 54 in relation to the design in accordance with the first embodiment of the flap 53, 54.

Figure 16B:
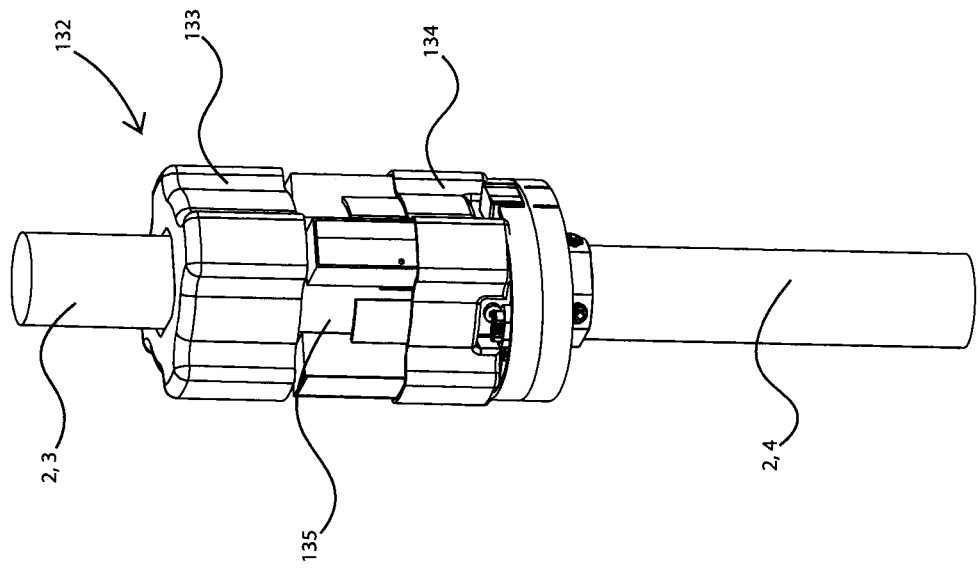
FIGS. 16A and 16B show an exemplifying battery pack connected to the coupling device.
Figure 16A:
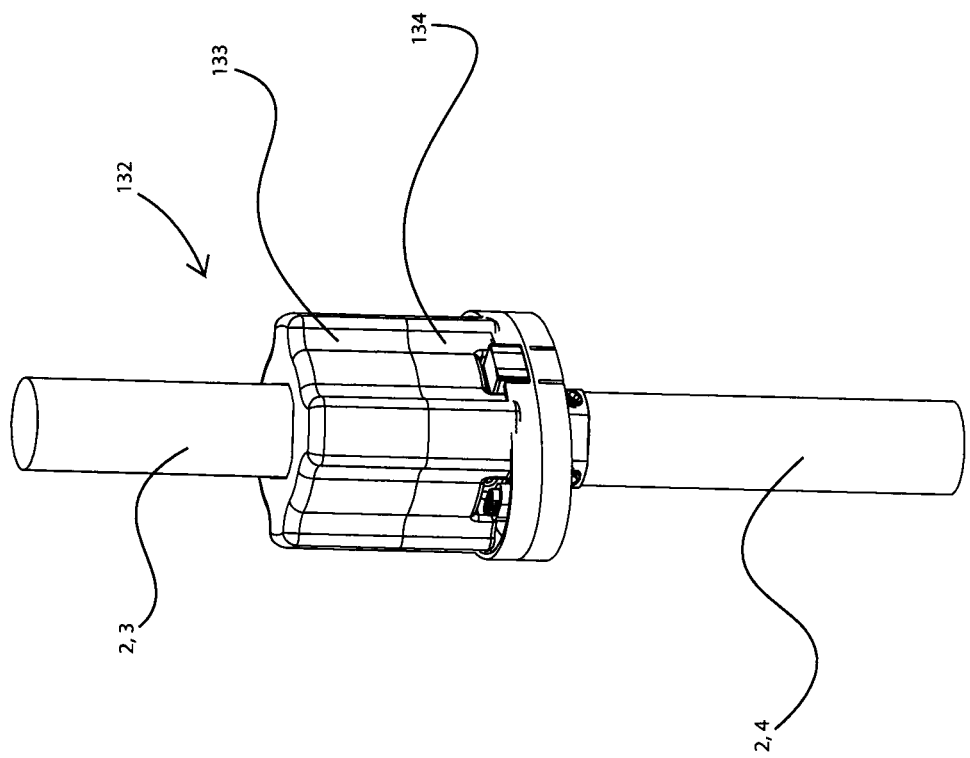

FIGS. 16A and 16B show that the coupling device 1 includes at least one battery pack (battery package) 132, for at least one accumulator, battery or similar. The shown battery pack (battery package) 132 is purely exemplifying and not limiting for the embodiment of the battery pack 132. The exemplifying battery pack (battery package) 132 includes at least one first half 133 and at least one second half 134 which can be connected and disconnected from each other. The first half 133 and the second half 134 include a centrally positioned through hole, hole or similar, in the axial direction through which part of the prosthesis is conveyed. When the first half 133 and the second half 134 are attached to each other, at least one internal space 135 is formed in which at least one accumulator is stored. In the exemplifying embodiment, the space 135 includes subspaces in which accumulators, batteries or the like are placed. The battery packs 132 form (shape) can vary extensively within the scope of the present invention.

Figure 17A:
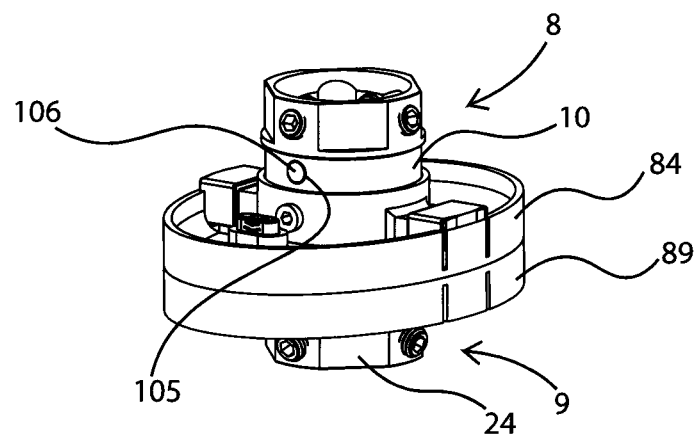
FIGS. 17A-17C shows a connected coupling device in accordance with the alternative embodiment.
Figure 17B:
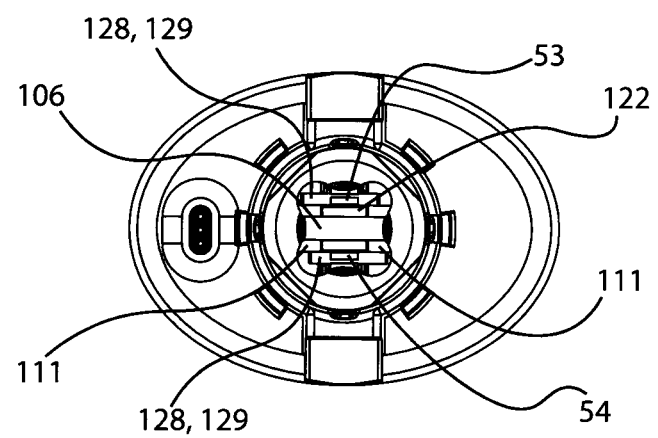
Figure 17C:
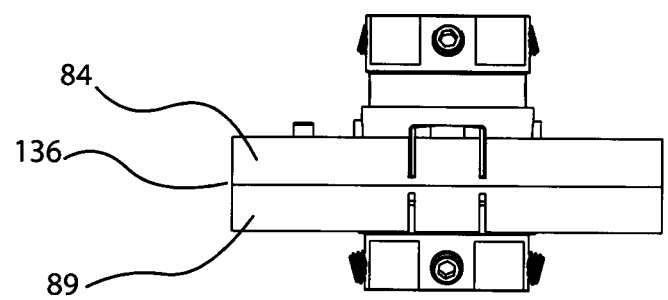

With reference to FIGS. 17A to 17C, an interconnected coupling device 1 is shown according to the alternative embodiment in different views. FIG. 17A shows the guide pin's 106 position when in a fixed position in the hole 105.

FIG. 17B shows the cooperation between the guide pin 106 and the recess 122. The figure also shows the flaps 53 and 54 with their related rods 129. The figure also shows the interplay between the positions.

With reference to FIG. 17C, an interconnected coupling device 1 is shown in the alternative embodiment where the holder's 84 and holder's 89 flat parts lie against each other and the dividing area 136 between the cosmetics 7 in the first part 3 of the prosthesis 2 and the second part 4 of the prosthesis 2.

In the detailed description of the present coupling device, details may be omitted which are obvious to a professional in the field of the coupling device. Such obvious details are included to the extent necessary to obtain an adequate function of the present coupling device.

Even though certain preferred embodiments of the coupling device are described in more detail, variations and modifications of the coupling device may be evident to professionals in the field of the invention. All such modifications and variations are considered to fall within the scope of subsequent claims.

In alternative embodiments, the coupling device can be used reversely, i.e. the first coupling part 8 is connected to the first part of the prosthesis and the second coupling part 9 is connected to the second part of the prosthesis. In addition, at least one of the female components of the pyramid coupling in the first coupling part 8 and the second coupling part 9 can consist of male parts.

ADVANTAGES OF THE INVENTION

The present invention achieves a number of advantages. The most obvious is that at least one of the problems described in the background is eliminated or substantially reduced. For example, the design of the present coupling device means that no tools are required to connect or disconnect the first coupling part and the second coupling part. An additional advantage of the present coupling device is that it includes an attachment device for cosmetics device.

The invention claimed is:

1. A coupling device, for connecting at least one first prosthetic part with at least one second prosthetic part of which at least one of the prosthetic parts is provided with, alternatively is suitable to be provided with, cosmetics;
said coupling device comprising at least one first coupling part connected to the first prosthesis part, alternatively the second prosthesis part, and at least one second coupling part connected to the second prosthesis part, alternatively the first prosthesis part;
said first coupling part comprising at least one first coupling member, comprising a female member, and the second coupling part comprising at least one second coupling member, comprising a male member;
said coupling members being suitable for connection to each other and in an interconnected position temporarily lock to each other with at least one locking device and that the coupling members are disengaged from each other with at least one disengaging device;
said locking device comprising at least one first flap comprising at least one first flap part suitable for temporary locking in a first track in the male member and at least one second flap comprising at least one second flap part which locks temporarily in a second track in the male member characterized in that the disengaging device comprises at least one first disengagement member and at least one second disengagement member which during disengagement of the coupling members is pressed against the first flap part of the first flap respectively being pressed against the second flap part of the second flap, whereby the first flap is pivoted out from engagement with the first track in the male member and the second flap is pivoted out of engagement with the second track in the male member and that the first coupling part comprises at least one first holder for cosmetics and that the second coupling part comprises at least one second holder for cosmetics and that cosmetics are attached to, alternatively integrated with, at least one of the first holder for cosmetics and the second holder for cosmetics.

2. A coupling device according to claim 1, wherein the female member has a square cross-section and that the male member has a square cross-section whose dimensions are conformed to one another in order to limit the play between them.

3. A coupling device according to claim 1, wherein the female member comprises at least one first surface and at least one second surface which are spaced at a distance from each other and that the male member has a square cross-section and that the distance between the first surface and the second surface conforms to the dimension of the male member.

4. A coupling device according to claim 1, wherein the female member is attached to, alternatively integrated with, an insert which is attached to the first coupling part.

5. A coupling device according to claim 4, wherein the flaps are attached to the insert.

6. A coupling device according to claim 1, wherein the coupling device comprises at least one damping device.

7. A coupling device according to claim 6, wherein the damping device comprises at least one material layer, placed between at least one surface in the insert of the first coupling part and at least one surface in the second coupling part.

8. A coupling device according to claim 7, wherein the cosmetics comprises at least one accumulator and that the first coupling part and the second coupling part include electrical connectors for energy transfer.

9. A coupling device according to claim 1, wherein the first disengagement member and the second disengagement member of the disengaging device are during disengagement maneuvered in the radial or essentially the radial direction of the second coupling part.

10. A coupling device according to claim 1, wherein the first holder for cosmetics comprises at least one tray-shaped part which comprises at least one first plate and a rim.

11. A coupling device according to claim 1, wherein the second holder for cosmetics comprises at least one tray-shaped part which comprises at least one second plate and a second edge.

12. A coupling device according to claim 1, wherein the male member at its free end comprises at least one steering device which comprises at least one recess suitable to engage with at least one transverse guide pin in the first coupling part, whereby the first coupling part and the second coupling part are mutually steered.

13. A coupling device according to claim 1, wherein the at least one first flap or the at least one second flap is pivotally arranged around an axis parallel to an axis of the at least one first prosthetic part and the at least one second prosthetic part.

* * * * *